(12) United States Patent
Byun et al.

(10) Patent No.: US 9,918,541 B2
(45) Date of Patent: Mar. 20, 2018

(54) WEARABLE DEVICE

(71) Applicant: Samsung Electronics Co., Ltd., Suwon-si, Gyeonggi-do (KR)

(72) Inventors: Dong-Hyun Byun, Suwon-si (KR); Dong-Hyeon Kim, Suwon-si (KR); Byoung-Uk Yoon, Hwaseong-si (KR); Young-Jin Yi, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 105 days.

(21) Appl. No.: 14/688,456

(22) Filed: Apr. 16, 2015

(65) Prior Publication Data

US 2015/0296963 A1 Oct. 22, 2015

(30) Foreign Application Priority Data

Apr. 22, 2014 (KR) .................. 10-2014-0047878

(51) Int. Cl.
| | |
|---|---|
| *A45F 5/02* | (2006.01) |
| *A61B 5/00* | (2006.01) |
| *G01C 22/00* | (2006.01) |
| *G04G 17/08* | (2006.01) |
| *G06F 1/16* | (2006.01) |

(Continued)

(52) U.S. Cl.
CPC .............. *A45F 5/02* (2013.01); *G04G 17/08* (2013.01); *A45F 2200/0516* (2013.01); *A45F 2200/0525* (2013.01); *A61B 5/1118* (2013.01); *A61B 5/6838* (2013.01); *A63B 24/0062* (2013.01); *G01C 22/006* (2013.01); *G06F 1/163* (2013.01)

(58) Field of Classification Search
CPC ..... A61B 5/6838; A61B 5/1118; A61B 5/025; A61B 5/1112; A61B 5/0205; A63B 24/0062; G01C 22/006; G06F 1/163; A45F 5/02; A45F 5/021; A45F 2200/0516; A45F 2200/0525; G04G 17/08
USPC .......... 361/679.02; 224/666, 668, 669, 670; 24/3.11
See application file for complete search history.

(56) References Cited

U.S. PATENT DOCUMENTS

| | | | | |
|---|---|---|---|---|
| 118,228 | A | * | 8/1871 | Frey ........................ A45F 5/021 188/77 R |
| 3,300,109 | A | * | 1/1967 | Clark .................... F41C 33/041 224/667 |
| 4,558,957 | A | | 12/1985 | Mock et al. |

(Continued)

FOREIGN PATENT DOCUMENTS

| | | |
|---|---|---|
| CN | 201562243 U | 8/2010 |
| CN | 202331047 U | 7/2012 |
| EP | 2 698 686 A2 | 2/2014 |

OTHER PUBLICATIONS

Brian Bennett, Fitbit One Review: Powerful Fitness Tracker, Weak Design, Apr. 30, 2013, pp. 1-4, CNET.

*Primary Examiner* — Justin Larson
(74) *Attorney, Agent, or Firm* — Jefferson IP Law, LLP

(57) ABSTRACT

A wearable device is provided. The wearable device includes a clip type wearing part including at least two first and second openings, and a body configured to fit to and to separate from the clip type wearing part. The clip type changeable wearing part includes a safe mounting part which is formed to have a shape of covering a circumference and bottom of the first opening, and to which the body is fitted, and at least a portion of the second opening is opened in the safe mounting part.

8 Claims, 49 Drawing Sheets

(51) Int. Cl.
*A61B 5/11* (2006.01)
*A63B 24/00* (2006.01)

(56) References Cited

U.S. PATENT DOCUMENTS

| | | | | |
|---|---|---|---|---|
| 4,742,503 A * | 5/1988 | Braun | G04B 37/1486 | 368/282 |
| 5,107,404 A * | 4/1992 | Tam | H04B 1/38 | 361/736 |
| 5,235,728 A * | 8/1993 | Nordberg | A45F 5/02 | 224/667 |
| 5,323,650 A * | 6/1994 | Fullen | A61B 5/1036 | 340/573.1 |
| 5,392,261 A * | 2/1995 | Hsu | G04B 37/1413 | 368/281 |
| 5,657,298 A * | 8/1997 | Choay | G04B 37/1413 | 368/276 |
| 5,899,370 A | 5/1999 | Bould | | |
| 5,983,458 A * | 11/1999 | Jackson | A45F 5/02 | 24/170 |
| 6,252,768 B1 * | 6/2001 | Lin | G06F 1/1616 | 248/624 |
| 6,264,079 B1 * | 7/2001 | Skaggs | F41C 33/0236 | 224/193 |
| 6,269,993 B1 * | 8/2001 | Ebejer | A45F 5/02 | 224/269 |
| 6,275,374 B1 * | 8/2001 | Shin | G06F 1/1616 | 361/679.55 |
| 6,743,030 B2 * | 6/2004 | Lin | H01R 31/065 | 439/131 |
| 6,889,879 B2 * | 5/2005 | Rivera | A45F 5/02 | 224/245 |
| 7,028,389 B2 * | 4/2006 | Chang | H05K 7/142 | 174/363 |
| D545,220 S | 6/2007 | Leung | | |
| 7,583,516 B2 * | 9/2009 | Lu | H05K 1/0271 | 361/807 |
| 7,793,361 B2 * | 9/2010 | Ishihara | A41D 1/002 | 2/170 |
| 8,345,412 B2 * | 1/2013 | Maravilla | A45F 5/00 | 224/219 |
| 8,386,008 B2 * | 2/2013 | Yuen | A61B 5/0002 | 600/382 |
| 8,408,436 B2 * | 4/2013 | Berry | A63B 24/00 | 224/176 |
| 8,506,158 B2 * | 8/2013 | Keung | A44C 5/0084 | 224/164 |
| 8,543,185 B2 * | 9/2013 | Yuen | A61B 5/0002 | 600/382 |
| 8,776,418 B1 * | 7/2014 | Martinez | G06F 15/00 | 150/147 |
| 8,868,377 B2 * | 10/2014 | Yuen | A61B 5/0002 | 702/160 |
| 8,919,019 B2 * | 12/2014 | Martinez | G06F 15/00 | 224/164 |
| 8,956,228 B2 * | 2/2015 | Shum | A43B 3/0005 | 463/1 |
| 9,004,329 B2 * | 4/2015 | Hsieh | G04G 17/08 | 224/169 |
| 9,141,087 B2 * | 9/2015 | Brown | G04F 10/00 | |
| 9,191,474 B2 * | 11/2015 | Song | H04M 1/0277 | |
| D752,579 S * | 3/2016 | Lee | D14/344 | |
| 9,291,845 B2 * | 3/2016 | Shin | H05K 5/0086 | |
| D768,028 S * | 10/2016 | Ling | D11/87 | |
| D772,730 S * | 11/2016 | Lai | D10/38 | |
| 9,486,167 B2 * | 11/2016 | Martinez | G06F 15/00 | |
| 9,515,692 B2 * | 12/2016 | Smith | H04B 1/385 | |
| 9,568,144 B2 * | 2/2017 | Pernu | F16M 11/041 | |
| 9,612,578 B2 * | 4/2017 | Huang | G04B 37/1486 | |
| 9,615,791 B2 * | 4/2017 | Zhang | A61B 5/681 | |
| 9,626,478 B2 * | 4/2017 | Armstrong | A61B 5/02405 | |
| 2005/0227811 A1 * | 10/2005 | Shum | A43B 3/0005 | 482/1 |
| 2009/0143689 A1 | 6/2009 | Berry et al. | | |
| 2012/0051015 A1 * | 3/2012 | Dabov | G06F 1/1656 | 361/760 |
| 2012/0081852 A1 | 4/2012 | Maravilla et al. | | |
| 2012/0083705 A1 | 4/2012 | Yuen et al. | | |
| 2013/0001263 A1 | 1/2013 | Kai | | |
| 2013/0032617 A1 | 2/2013 | Adelman et al. | | |
| 2014/0028546 A1 | 1/2014 | Jeon et al. | | |
| 2015/0103475 A1 * | 4/2015 | Yang | G06F 1/1658 | 361/679.02 |
| 2016/0317086 A1 * | 11/2016 | Smith | A61B 5/681 | |

* cited by examiner

WEARABLE DEVICE

CROSS-REFERENCE TO RELATED APPLICATION(S)

This application claims the benefit under 35 U.S.C. § 119(a) of a Korean patent application filed on Apr. 22, 2014 in the Korean Intellectual Property Office and assigned Serial number 10-2014-0047878, the entire disclosure of which is hereby incorporated by reference.

TECHNICAL FIELD

The present disclosure relates to an electronic device worn on the human body.

BACKGROUND

In a method of carrying electronic devices, users may carry the electronic devices in their pockets or bags and the like, or carry the electronic devices by hand, or may wear the electronic devices in certain positions on the human body. Wearable devices are worn on various portions of the human body for use.

In addition, in a wearable device design method of the related art, hooks and bosses are installed in a housing provided at upper and lower sides of a Printed Circuit Board (PCB) and these hooks and bosses are assembled/coupled to one another.

The above information is presented as background information only to assist with an understanding of the present disclosure. No determination has been made, and no assertion is made, as to whether any of the above might be applicable as prior art with regard to the present disclosure.

SUMMARY

Also, in the wearable device design method of the related art, a structure of installing the hooks and bosses in the housing and assembling/coupling these hooks and bosses to one another is simple in design and manufacture. However, because this simple structure essentially requires uniting structure installation, it acts as a physical limit to the miniaturization of a simple wearable device.

Aspects of the present disclosure are to address at least the above-mentioned problems and/or disadvantages and to provide at least the advantages described below. Accordingly, an aspect of the present disclosure is to provide a wearable device capable of seeking efficient electronic component arrangement within a body.

Another aspect of the present disclosure is to provide a wearable device being advantageous to slimming and simplification.

Another aspect of the present disclosure is to provide a wearable device capable of attaching and detaching a body and a connector, thereby making possible replacement according to user's tastes.

Another aspect of the present disclosure is to provide a wearable device providing directivity of coupling of a body.

Another aspect of the present disclosure is to provide a wearable device providing an appearance design method for minimizing the wearable device, a structure of mounting electronic components within the wearable device, and a structure of applying an electronic equipment accessory diversely and conveniently.

In accordance with an aspect of the present disclosure, a wearable device is provided. The wearable device includes a changeable wearing part having an opening, and a body configured to tightly fit to and separate from the opening. The changeable wearing part is formed to have a shape of covering a lateral surface circumference of the opening and a bottom of the opening, and includes a safe mounting part elastically deformed.

In accordance with another aspect of the present disclosure, a wearable device is provided. The wearable device includes a clip type wearing part including at least two first and second openings, and a body configured to fit to and to separate from the clip type wearing part. The clip type wearing part includes a safe mounting part which is formed to have a shape of covering a circumference and bottom of the first opening, and to which the body is fitted. At least a portion of the second opening is opened in the safe mounting part.

In accordance with another aspect of the present disclosure, a wearable device having at least one key is provided. The wearable device includes a front case, a rear case, and a connection case. Boundary portions among the cases are coupled to one another by ultrasonic fusion.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
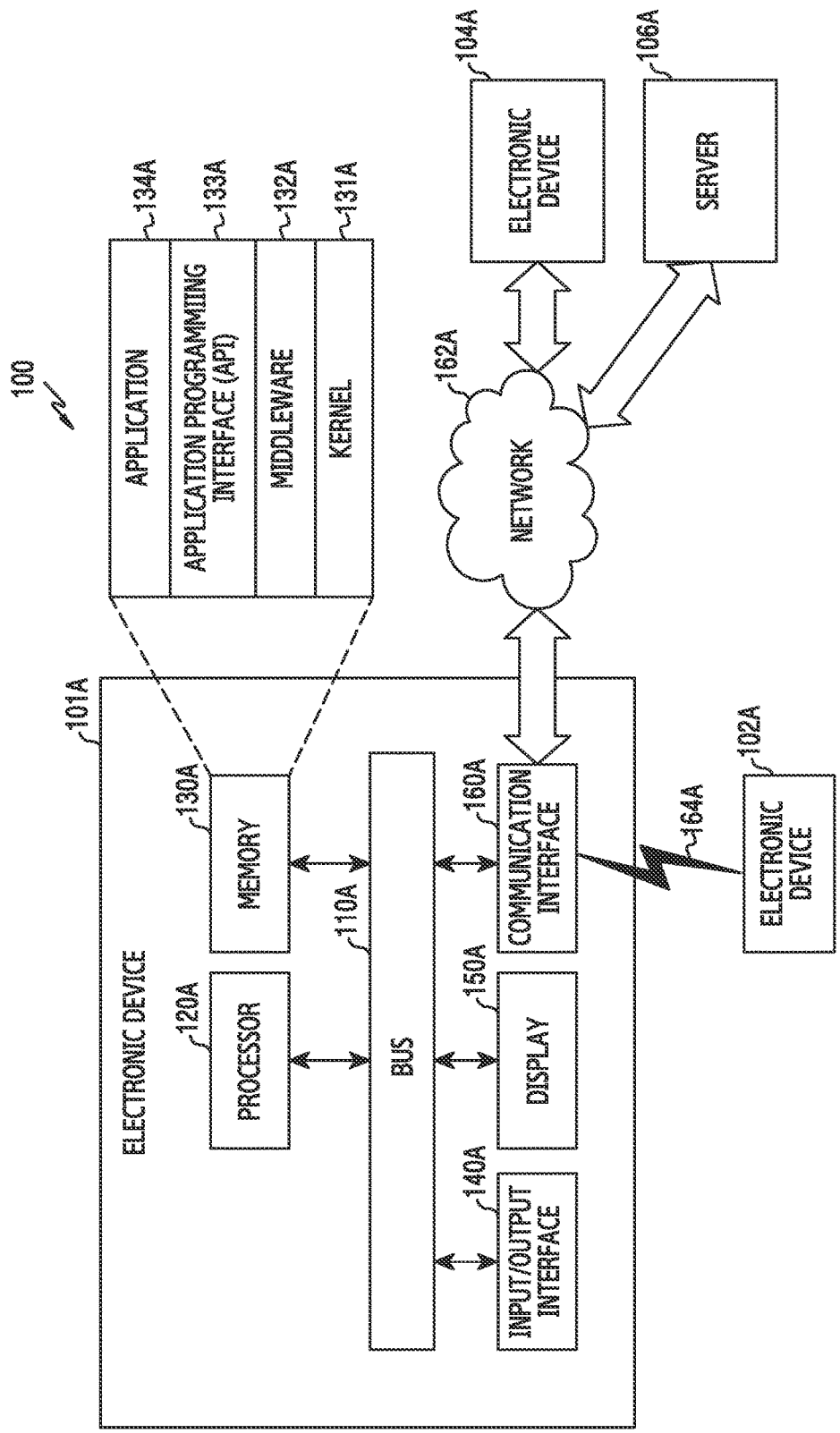
FIG. 1 illustrates a network environment including an electronic device according to various embodiments of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein may be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In a description of the present disclosure, the term "substantially or approximately" represents that a cited characteristic, parameter or value is not needed to be accurately achieved, and a variation or change including an allowable error, a measurement error, a measurement accuracy limit, and other elements known to those skilled in the art, and a characteristic may occur to the extent of not excepting effects intended to be provided.

The expressions "comprise", "may comprise" or the like usable in the present disclosure indicate the existence of disclosed corresponding functions, operations, constituent elements or the like, and do not limit additional one or more functions, operations, constituent elements or the like. In addition, in the present disclosure, the terms "comprise", "have" or the like are to designate the existence of features stated in the specification, numerals, operations, constituent elements, components, or a combination of them, and it should be understood that the terms "comprise", "have" or the like are not to previously exclude the possibility of existence or addition of one or more other features, numerals, operations, constituent elements, components, or combinations of them.

In the present disclosure, the expressions such as "or" and the like include any and all combinations of words enumerated together. For example, "A or B" may include A, or may include B, or may include all A and B.

The expressions "1st", "2nd", "first", "second" or the like used in the present disclosure may modify various constituent elements of the present disclosure, but do not intend to limit the corresponding constituent elements. For example, the expressions do not limit the order and/or importance and the like of the corresponding constituent elements. The expressions may be used to distinguish one constituent element from another constituent element. For example, all of a first user device and a second user device are user devices, and represent different user devices. For example, a first constituent element may be named as a second constituent element without departing from the scope of right of the present disclosure. Likely, even a second constituent element may be named as a first constituent element.

When it is mentioned that any constituent element is "connected" or "accessed" to another constituent element, the any constituent element may be directly connected or accessed to the another constituent element, but it should be understood that new other constituent element may also exist between the any constituent element and the another constituent element. In contrast, when it is mentioned that any constituent element is "directly connected" or "directly accessed" to another constituent element, it should be understood that no new other constituent element exists between the any constituent element and the another constituent element.

Unless defined otherwise, all the terms used herein including the technological or scientific terms have the same meaning as those commonly understood by a person having ordinary knowledge in the art which the present disclosure belongs to. The terms as defined in a general dictionary should be interpreted as having the same meanings as the contextual meanings of a related technology, and are not interpreted as having ideal or excessively formal meanings unless defined clearly in the present disclosure.

An electronic device according to the present disclosure may be a device including a telecommunication function. For example, the electronic device may include at least one of a smart phone, a tablet Personal Computer (PC), a mobile phone, a video phone, an electronic book (e-book) reader, a desktop PC, a laptop PC, a netbook computer, a Personal Digital Assistant (PDA), a Portable Multimedia Player (PMP), an Moving Picture Experts Group (MPEG-1 or MPEG-2) Audio Layer 3 (MP3) player, a mobile medical instrument, a camera, or a wearable device (e.g., a Head Mounted Display (HMD) such as electronic glasses, electronic clothes, an electronic bracelet, an electronic necklace, an appcessory, an electronic tattoo, or a smart watch).

Below, an electronic device according to various embodiments of the present disclosure will be described with reference to the accompanying drawings. The term 'user' used in the various embodiments of the present disclosure may denote a person who uses the electronic device or a device (e.g., an artificial intelligent electronic device) which uses the electronic device.

FIG. 1 illustrates a network environment including an electronic device according to various embodiments of the present disclosure.

Referring to FIG. 1, a network environment 100 may include an electronic device 101A. The electronic device 101A may include a bus 110A, a processor 120A, a memory 130A, an input/output interface 140A, a display 150A, and a communication interface 160A.

The bus 110A may be a circuit connecting the aforementioned constituent elements with one another and forwarding a communication signal (e.g., a control message) between the aforementioned constituent elements.

The processor 120A may, for example, receive instructions from the aforementioned other constituent elements (e.g., the memory 130A, the input/output interface 140A, the display 150A, and the communication interface 160A) through the bus 110A, and decipher the received instructions, and execute operation or data processing according to the deciphered instructions.

The memory 130A may store instructions or data that are received from the processor 120A or the other constituent elements (e.g., the input/output interface 140A, the display 150A, and the communication interface 160) or is generated by the processor 120A or the other constituent elements. The memory 130A may, for example, include programming modules such as a kernel 131A, a middleware 132A, an Application Programming Interface (API) 133A, an application 134A, or the like. The aforementioned programming modules each may be comprised of software, firmware, hardware or a combination of at least two or more of them.

The kernel 131A may control or manage system resources (e.g., the bus 110A, the processor 120A, the memory 130A or the like) used for executing operations or functions implemented in the remnant other programming modules, for example, the middleware 132A, the API 133A, or the application 134A. In addition, the kernel 131A may provide an interface enabling the middleware 132A, the API 133A, or the application 134A to connect and control or manage the individual constituent element of the electronic device 101A.

The middleware 132A may perform a relay role of enabling the API 133A or the application 134A to communicate and exchange data with the kernel 131A. In addition, in relation to work requests received from the application 134A, the middleware 132A may, for example, perform control (e.g., scheduling or load balancing) for the work requests using a method of allocating at least one application among the applications 134A priority order capable of using the system resources (e.g., the bus 110A, the processor 120A, the memory 130A or the like) of the electronic device 101A.

The API 133A is an interface enabling the application 134A to control a function provided by the kernel 131A or the middleware 132A. The API 133A may, for example, include at least one interface or function (e.g., an instruction) for file control, window control, picture processing, character control or the like.

According to various embodiments of the present disclosure, the application 134A may include a Short Message Service (SMS)/Multimedia Message Service (MMS) application, an electronic mail (e-mail) application, a calendar application, an alarm application, a health care application (e.g., an application measuring a momentum, a blood sugar or the like), an environment information application (e.g., an application providing air pressure, humidity, temperature information or the like) or the like. Additionally or alternatively, the application 134A may be an application related with information exchange between the electronic device 101A and an external electronic device (e.g., an external electronic device 102A or another external electronic device 104A). The application related with the information exchange may include, for example, a notification relay application for relaying specific information to the external electronic device, or a device management application for managing the external electronic device.

For example, the notification relay application may include a function of relaying notification information generated in other applications (e.g., the SMS/MMS application, the e-mail application, the health care application, the environment information application or the like) of the electronic device 101A, to the external electronic device (e.g., the external electronic device 102A or the other electronic device 104A). Additionally or alternatively, the notification relay application may, for example, receive notification information from the external electronic device (e.g., the external electronic device 102A or the other external electronic device 104A) and provide the received notification information to a user. The device management application may, for example, manage (e.g., install, delete or update) a function (e.g., turn-on/turn-off of the external electronic device (or some constituent components thereof), or adjustment of a brightness (or resolution) of a display) of at least a part of the external electronic device (e.g., the external electronic device 102A or the other external electronic device 104A) communicating with the electronic device 101A, an application operating in the external electronic device, or a service (e.g., a telephony service or a message service) provided in the external electronic device.

According to various embodiments of the present disclosure, the application 134A may include an application designated according to an attribute (e.g., the kind of electronic device) of the external electronic device (e.g., the external electronic device 102A or the other external electronic device 104A). For example, when the external electronic device is an MP3 player, the application 134A may include an application related with music playback. Similarly, when the external electronic device is a mobile medical instrument, the application 134A may include an application related with health care. According to an embodiment of the present disclosure, the application 134A may include at least one of an application designated to the electronic device 101A or an application received from the external electronic device (e.g., the server 106A or the external electronic device 102A or the other external electronic device 104A).

The input/output interface 140A may forward an instruction or data, which is inputted from a user through a sensor (e.g., an acceleration sensor, a gyro sensor) or an input device (e.g., a keyboard or a touch screen), for example, to the processor 120A, the memory 130A and the communication interface 160A through the bus 110A. For example, the input/output interface 140A may provide data about a user's touch inputted through the touch screen, to the processor 120A. In addition, the input/output interface 140A may, for example, output through an input/output device (e.g., a speaker or a display) an instruction or data which is received from the processor 120A, the memory 130A, or the communication interface 160A through the bus 110A. For example, the input/output interface 140A may output voice data, which is processed through the processor 120A, to the user through the speaker.

The display 150A may display various information (e.g., multimedia data, text data, or the like) to a user.

The communication interface 160A may connect communication between the electronic device 101A and the external device (e.g., the external electronic device 102A or the other external electronic device 104A or the server 106A). For example, the communication interface 160A may support a network communication 162A (e.g., Internet, a Local Area Network (LAN), a Wireless Area Network (WAN), a telecommunication network, a cellular network, a satellite network, or a Plain Old Telephone Service (POTS)), a short-range communication 164A (e.g., Wi-Fi, Bluetooth (BT), Near Field Communication (NFC)), or a wired communication (e.g., a Universe Serial Bus (USB), a High Definition Multimedia Interface (HDMI), a Recommended Standard-232 (RS-232), or a POTS). According to an embodiment of the present disclosure, a protocol (e.g., a short-range communication protocol, a network communication protocol, or a wired communication protocol) for communication between the electronic device 101A and an external device may be supported in at least one of the application 134A or the middleware 132A. Each of the external electronic devices 102A and 104A may be the same (e.g., same-type) device as the electronic device 101A or a different (e.g., different-type) device.

A construction of a wearable device according to various embodiments of the present disclosure is described with reference to FIGS. 2 to 10.

Figure 2:
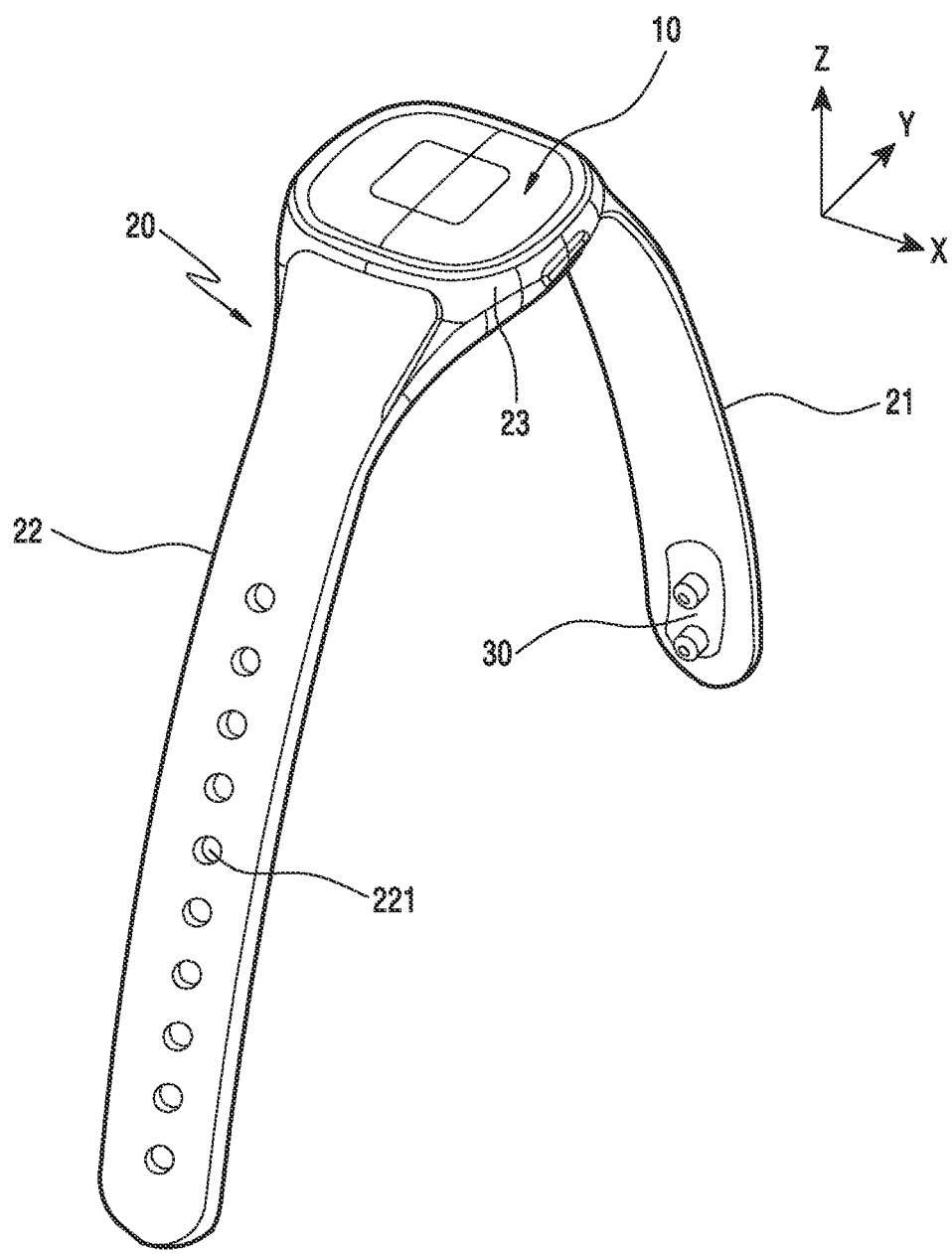
FIG. 2 is a perspective diagram illustrating a wearable device coupling a body and a wearing part according to various embodiments of the present disclosure.

FIG. 2 is a perspective diagram illustrating a wearable device coupling a body and a wearing part according to various embodiments of the present disclosure.

Figure 3:
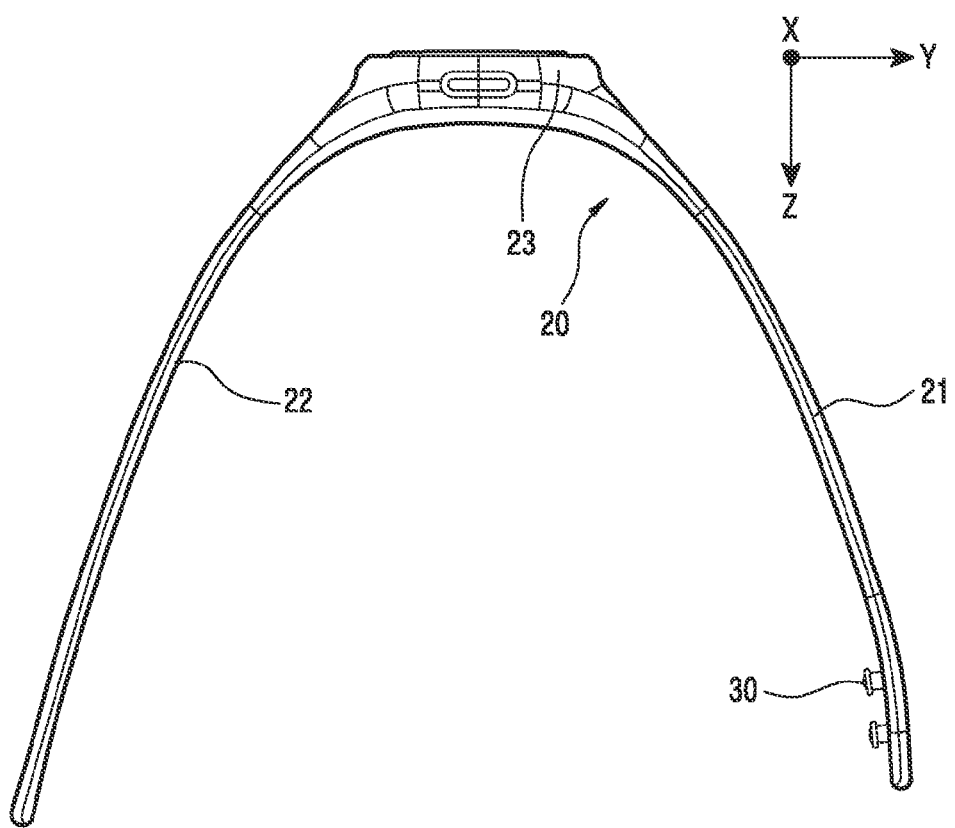
FIG. 3 is a side diagram illustrating a wearable device coupling a body and a wearing part according to various embodiments of the present disclosure.

FIG. 3 is a side diagram illustrating a wearable device coupling the body and the wearing part according to various embodiments of the present disclosure.

Figure 4:
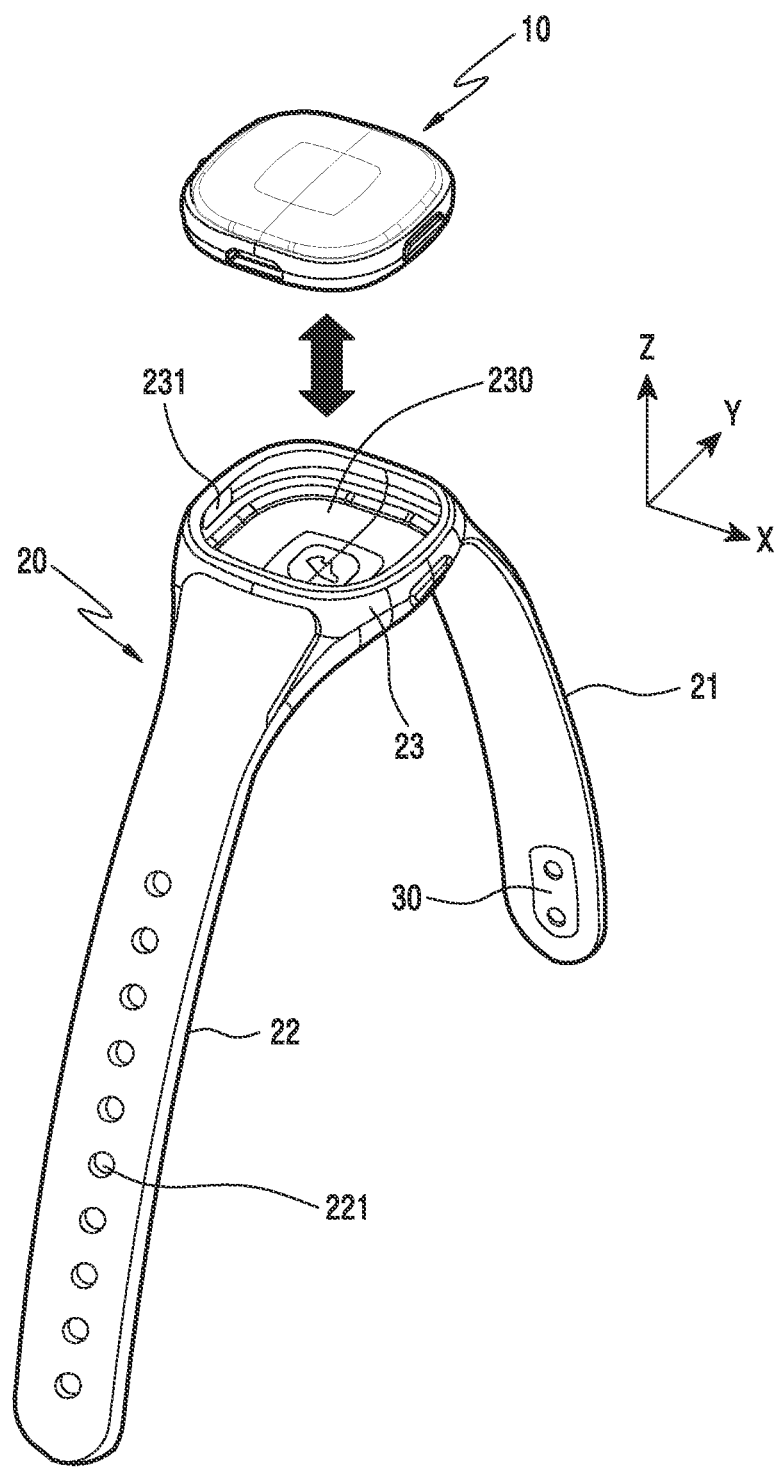
FIG. 4 is a perspective diagram illustrating a wearable device separating a body and a wearing part according to various embodiments of the present disclosure.

FIG. 4 is a perspective diagram illustrating a wearable device separating the body and the wearing part according to various embodiments of the present disclosure.

Referring to FIGS. 2 to 4, three-dimensional X/Y/Z rectangular coordinate systems are shown in the respective figures. 'Z axis' is vertical orientation and represents up/down orientation (i.e., thickness orientation) of a body 10. 'X axis' is first horizontal orientation and represents horizontal orientation of the body 10. 'Y axis' is second horizontal orientation being vertical to the first horizontal orientation and represents vertical orientation of the body 10.

The wearable device according to various embodiments of the present disclosure, which is an electronic device worn on the human body, is for example an electronic device convenient for wearing on the wrist such as a wristwatch or a bracelet, a communication device, or an assistant medical instrument. However, the wearable device according to the various embodiments of the present disclosure is not limited to being worn on the wrist. For instance, the wearable device according to the various embodiments of the present disclosure is identically applicable to a curved portion of the human body. As one example of the human body portion having such a curvature among the human body, there may be the wrist, the ankle, or the like. In addition, it should be noted that, if a wearing part 20 is constructed variously, the wearable device according to the various embodiments of the present disclosure may be stably worn on various portions of the human body, or be worn on clothes of the human body or articles carried by users.

The wearable device according to the various embodiments of the present disclosure may include the body 10 (i.e., function device part), the wearing part 20 (including a band or strap), and a uniting tool (e.g., a uniting device of hard materials such as a buckle). The body 10 may be configured to be forcedly coupled to or separable from the wearing part 20.

The body 10 according to the various embodiments of the present disclosure may arrange a key for inputting various kinds of information, a sensor, an interface part, and a component for notification occurrence. In addition, additionally, though not illustrated in the drawings, the body 10 may arrange a display for displaying various information, a touch input part, a vibration element, and the like. The body 10 may have a roughly square appearance having a thickness. However, the body 10 is not limited to a shape of the roughly square appearance, and may make various modifications. For instance, the body 10 may be configured to have a curved surface as well as a flat surface as an upper surface. The curved surface may be configured to have a curvature. Because the body 10 takes charge of a function of a housing forming an appearance, the body 10 and the housing may be stated in combination.

The wearing part 20 according to various embodiments of the present disclosure may be formed of elastic materials. Thus, the wearing part 20 may make it possible to stably wear the body 10 on the human body and may be closely adhered to the human body skin. In addition, because the wearing part 20 is changeable, the wearing part 20 takes charge of a function of an accessory exhibiting user's individuality or taste. However, a portion 23 (i.e., safe mounting part) of the wearing part 20 coupled to the body 10 is configured to make elastic deformation possible, and a wearing surface portion closely adhered to the human body may not be formed of elastic materials, for instance, may be formed of metal materials. The wearing part 20 may include an opening 230 opened in up orientation and closed in down orientation, a safe mounting part 23 elastically deformed along a circumference of the opening 230, a uniting tool 30, a wearing hole 221 and a pair of straps 21 and 22. The wearing part 20 may include an elastic member (i.e., safe mounting part) around the opening 230. The wearing part 20 may include a portion for, when the body 10 is fitted to the wearing part 20, closely adhering at least a part of the elastic safe mounting part 23 of the wearing part 20 to a circumference of a lateral surface of the body 10. In addition, the wearing part 20 may be formed of two or more materials, not one material. That is, the safe mounting part 23 and the straps 21 and 22 constructing the wearing part 20 may be formed of different materials. Accordingly, the safe mounting part 23 and the first and second straps 21 and 22 may have different elastic deformations.

Referring to FIG. 4, the opening 230 according to various embodiments of the present disclosure is a recess for coupling the body 10, and is of a shape in which a circumference and bottom of the opening 230 are surrounded by the safe mounting part 23. The opening 230 according to the present embodiment of the present disclosure may be configured to have a roughly square shape having a thickness. In addition, the safe mounting part 23 may have an additional opening 231.

The additional opening 231 may be an opening for exposing a slide key described later to the external of the safe mounting part 23. In addition, the body 10 may be configured to have a roughly square shape slightly smaller than the opening 230 of the safe mounting part 23 and thus, the body 10 may be tightly fitted to the safe mounting part 23.

In addition, the wearing part 20 may include a uniting tool 30 (e.g., it may be denoted as a 'buckle part') for weaving and uniting respective both ends of the first and second straps 21 and 22.

In addition, the wearable device according to an embodiment of the present disclosure includes a detachable structure in which the body 10 is coupled and separated mechanically. The detachable structure of the wearable device may include an appearance shape of the body 10, a shape of the opening 230 provided in the safe mounting part 23, and materials of the safe mounting part 23. The detachable structure of the wearable device may have an additional coupling structure. The opening 230 of the safe mounting part 23 is configured to have a size (i.e., horizontal, vertical, and thickness sizes) slightly smaller than the body 10. Thus, if the body 10 is forcedly coupled to the opening 230 of the safe mounting part 23, the body 10 may be tightly coupled to the safe mounting part 23. The safe mounting part 23 is elastically deformed and the opening 230 is configured to have a volume of coupling or separating the body 10 by a forced user's force, thereby making possible an attachment and detachment operation of the body 10. Specifically, the safe mounting part 23 is of a shape of having an inner surface capable of adhering to, specifically, covering a circumference (i.e., a connection case described later) of the body 10.

In addition, the body 10 may be forcedly fitted or separable with directivity from the wearing part 20, by means of a shape of the body 10 and a structure of the safe mounting part 23. The safe mounting part 23 may be configured to have a shape of covering the whole side circumference of the body 10 and a bottom surface thereof. A bottom surface of the safe mounting part 23 is not limited to a closed shape. That is, at least a portion of the bottom surface of the safe mounting part 23 may be configured to be opened. If the body 10 has a bio sensor (not shown), at least the portion of the bottom surface of the safe mounting part 23 may be configured to have an opening.

Because the wearing part 20 according to various embodiments of the present disclosure has a changeable structure, the wearing part 20 is changeable anytime according to user's tastes if being implemented in various designs and colors.

Figure 5:
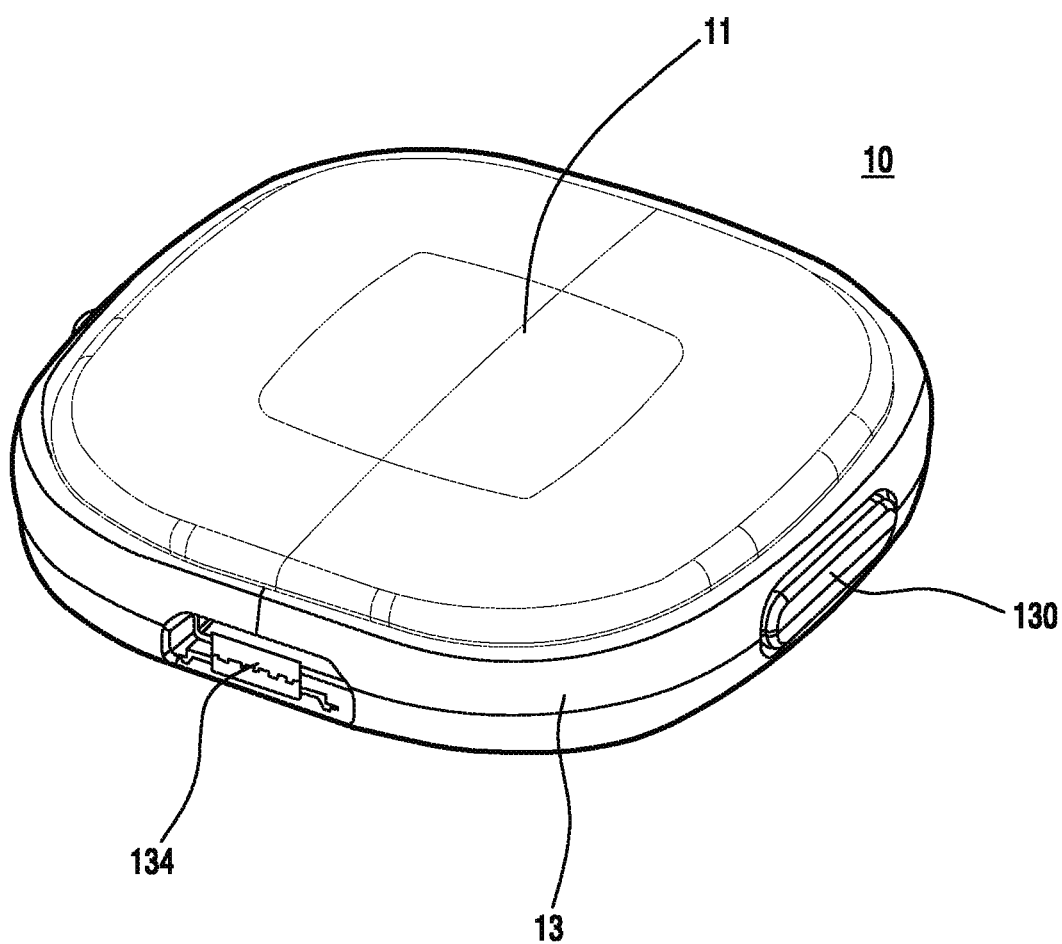
FIGS. 5 and 6 are perspective diagrams illustrating states of viewing a body of a wearable device in different orientations, respectively, according to various embodiments of the present disclosure.
Figure 6:
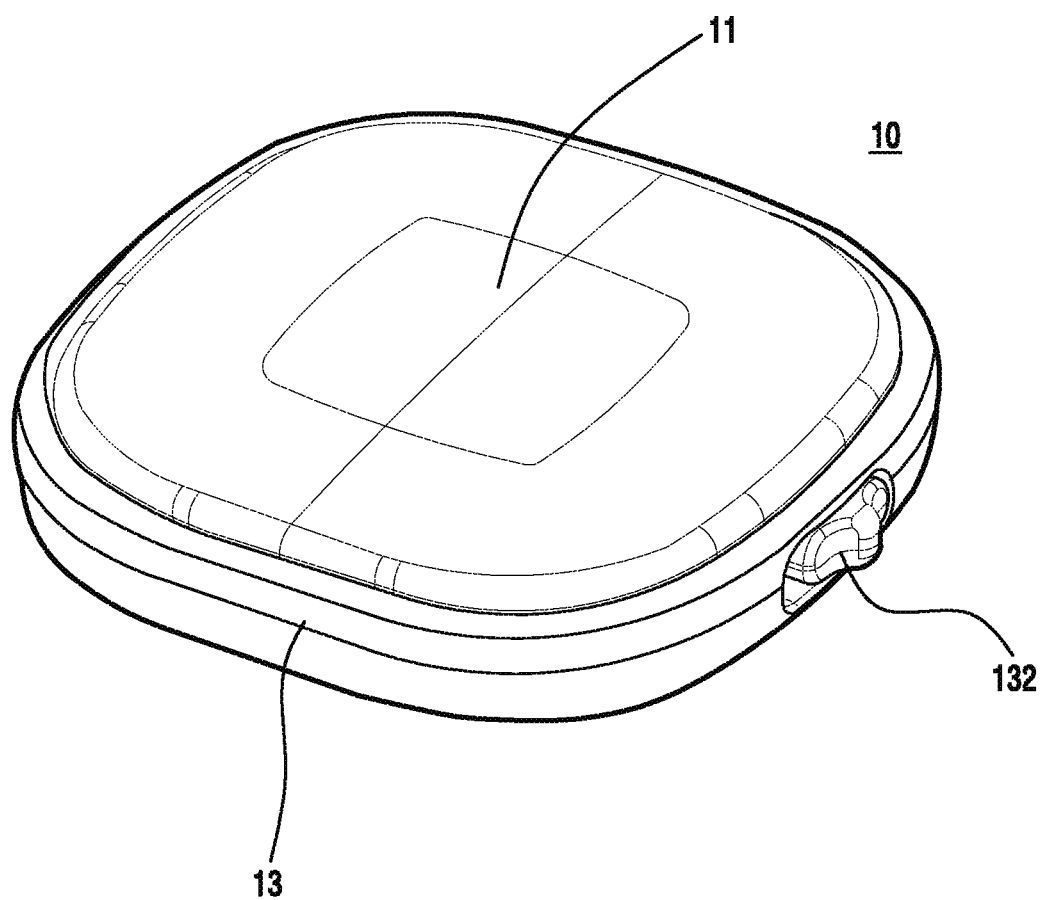

FIGS. 5 and 6 are perspective diagrams illustrating states of viewing a body of a wearable device in different orientations, respectively, according to various embodiments of the present disclosure.

Figure 7:
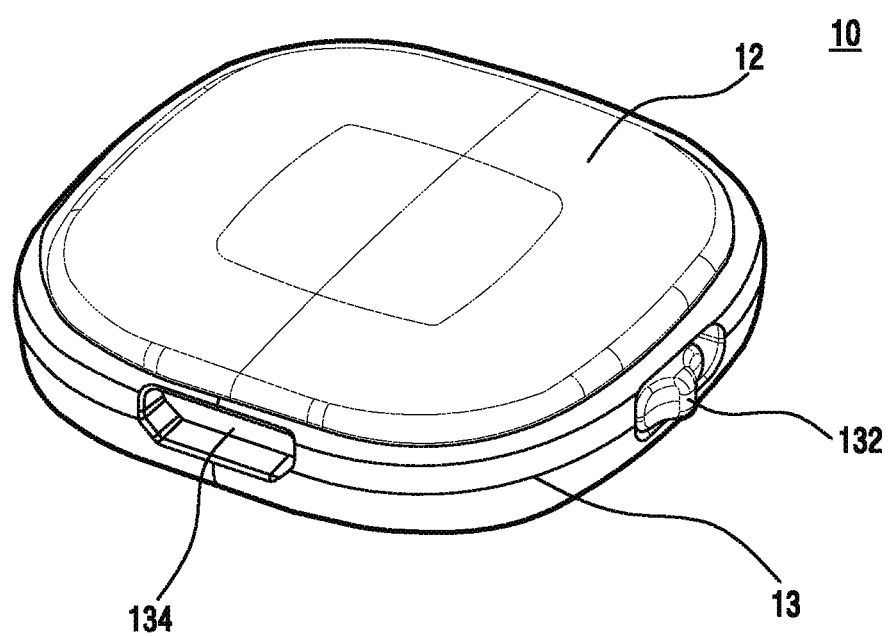
FIG. 7 is a perspective diagram illustrating a rear surface of a body of a wearable device according to various embodiments of the present disclosure.

FIG. 7 is a perspective diagram illustrating a rear surface of the body of the wearable device according to various embodiments of the present disclosure.

Referring to FIGS. 5 to 7, the body 10 according to various embodiments of the present disclosure may consist of three cases 11, 12, and 13. The three cases 11, 12, and 13 may be coupled with one another and take charge of a function and appearance of a housing of the body 10. The body 10 may include the front case 11, the connection case 13, and the rear case 12 which are shown to a user when the body 10 is coupled to the wearing part 20. The front case 11 may include a display, and may be constructed as a transparent or semitransparent case. In addition, the front case 11 may be configured to have a curvature, or may not have the curvature. If the front case 11 has the curvature, the front case 11 may be a curved display. If the front case 11 does not have the curvature, the front case 11 may be a flat display. The display may include a touch screen, a Liquid Crystal Display (LCD), an Organic Light Emitting Diode (OLED), and the like.

If the front case 11 is formed of transparent or semitransparent synthetic resins, light emitted from the interior of the body 10 becomes visible. Thus, a user may check the emitted light and recognize information meant by the light. Though described later, light emitted from an LED may be displayed through at least a portion of the front case 11. In this case, at least the portion of the front case 11 may take charge of a function of light wave guide.

The connection case 13 may include physically one or a plurality of keys 130 and 132. FIG. 5 illustrates one example of arranging the first side key 130 operated by a user's physical press motion, and FIG. 6 illustrates one example of arranging the second side key 132 (i.e., slide key) configured to face the first side key 130. The connection case 13 is configured to have a curved surface which is slightly convexed outwards. Thus, when the body 10 is fully coupled to the safe mounting part, the connection case 13 of the body 10 gives help for prevention of separation of the body 10. An interface part connector 134 may be arranged in a circumference surface between the first and second side keys 130 and 132.

The rear case 12 of the body 10 illustrated in FIG. 7 is provided to a battery side.

Figure 8:
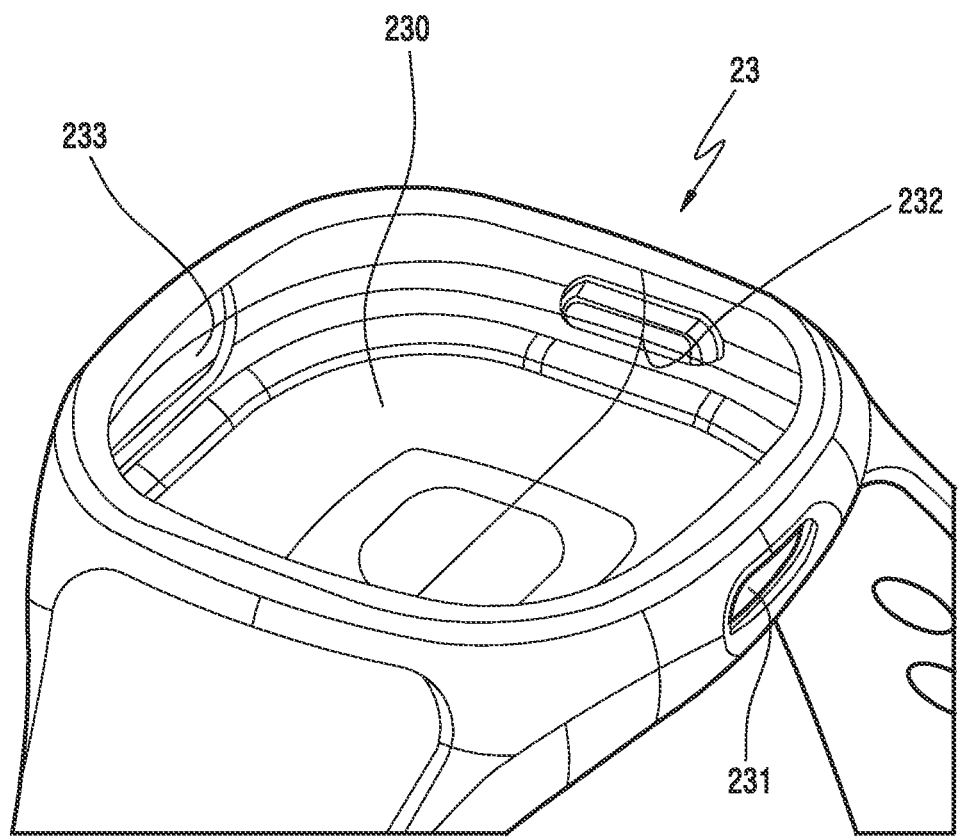
FIG. 8 is a perspective diagram illustrating a safe mounting part of a wearing part of a wearable device according to various embodiments of the present disclosure.

FIG. 8 is a perspective diagram illustrating a safe mounting part of a wearing part of a wearable device according to various embodiments of the present disclosure.

Figure 9:
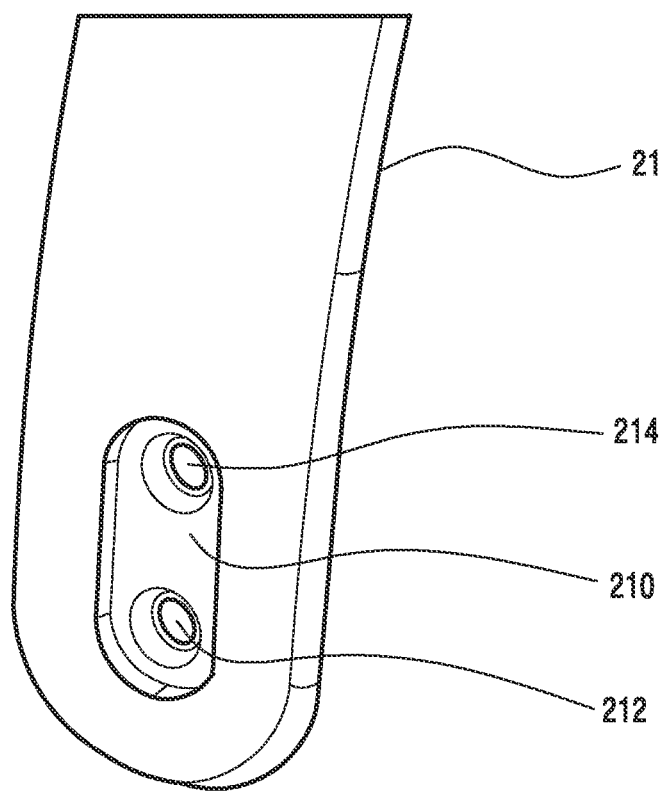
FIG. 9 is a perspective diagram illustrating a portion of a first strap of a wearing part according to various embodiments of the present disclosure.

FIG. 9 is a perspective diagram illustrating a portion of a first strap of a wearing part according to various embodiments of the present disclosure.

Figure 10:
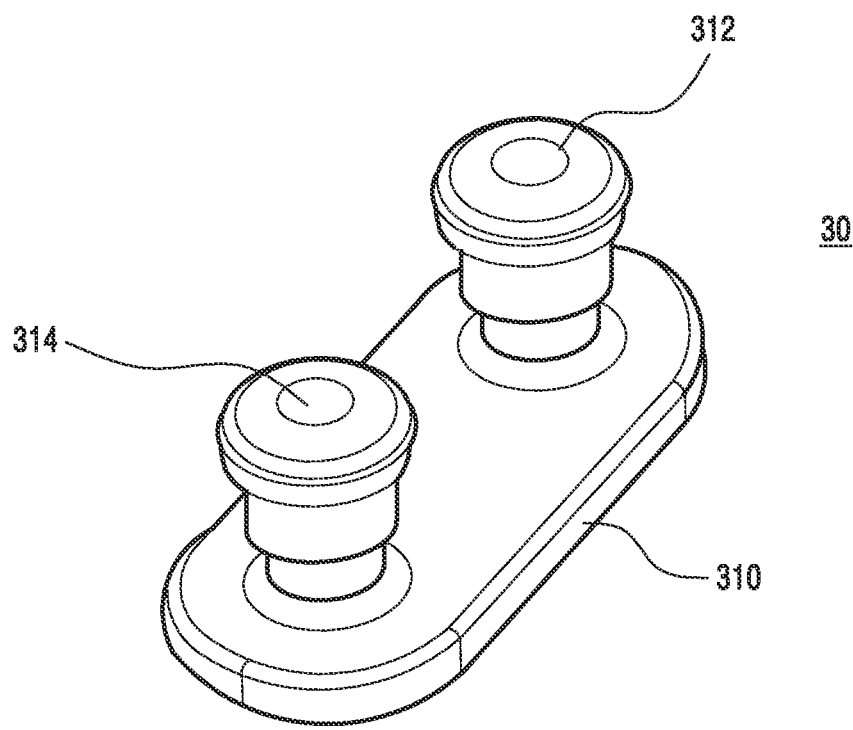
FIG. 10 is a perspective diagram illustrating a uniting tool coupled to a first strap of a wearing part according to various embodiments of the present disclosure.

FIG. 10 is a perspective diagram illustrating a uniting tool coupled to a first strap of a wearing part according to various embodiments of the present disclosure. Constructions of a safe mounting part and uniting tool according to various embodiments of the present disclosure are described below with reference to FIGS. 8 to 10.

Referring to FIG. 8, a safe mounting part 23 of the wearing part may be configured to have a shape capable of covering a circumference surface and bottom surface of the body while closely adhering to the circumference surface and bottom surface of the body. A coupling part 232 may be provided in an inner surface of the safe mounting part 23 and may couple with the interface part connector 134 (shown in FIGS. 5 and 7) of the body. If the interface part connector 134 of the body is coupled to the coupling part 232 of the safe mounting part 23, the interface part connector 134 may help coupling the body to the safe mounting part 23 by means of a coupling structure between the coupling part 232 and the interface part connector 134. The coupling part 232 may be constructed one or plural, and may be constructed as a protrusion shape matching with the interface part connector 134. The opening 230 may be an opening space for housing the body, and the additional opening 231 may be a hole for exposing the second side key 132 (shown in FIG. 7) to the exterior. Reference numeral 233 denotes a key press part formed in the safe mounting part 23. If the key press part 233 of the safe mounting part 23 is pressed, the first side key of the body may be pressed.

Referring to FIGS. 9 and 10, the first strap 21 of the wearing part may include a uniting tool safe mounting part 210 and one or a plurality of wearing openings 212 and 214 in an end region thereof. The uniting tool safe mounting part 210 installs the uniting tool 30 (shown in FIG. 10) described later. The uniting tool safe mounting part 210, which is of a groove shape of coupling with a base 310 of the uniting tool 30, is recessed to a certain depth from an outer surface of the first strap 21. The wearing openings 212 and 214 may be holes which a guide pin 312 and a catching pin 314 (described later) pass through.

Referring to FIG. 10, the uniting tool 30 according to various embodiments of the present disclosure is a coupling member formed of metal materials, or synthetic resins of rigid materials or elastic flexible materials. The uniting tool 30 includes the base 310, the guide pin 312, and one or a plurality of catching pins 314. The uniting tool 30 may be installed in the end region of the first strap of the wearing part, and may bind both ends of the first and second straps together.

In addition, the guide pin 312 may be replaced with the catching pin 314. One example in which the uniting tool 30 includes one guide pin 312 and one catching pin 314 is illustrated in FIG. 10.

The uniting tool 30 may include the base 310, one or plurality of guide pins 312, and the one or plurality of catching pins 314 having the same or different shape as the guide pins 312. The uniting tool 30 is changeable by a detachable structure of the uniting tool safe mounting part. Accordingly, the uniting tool 30 according to various embodiments of the present disclosure may be manufactured by various materials or colors.

In an embodiment of the present disclosure, the uniting tool 30 illustrated in FIG. 10 includes one guide pin 312 and one catching pin 314. But, the uniting tool 30 may consist of two guide pins and one catching pin, and may consist of one guide pin and two catching pins. Regarding the arrangement position of the guide pin 312 and the catching pin 314, the catching pin 314 may be arranged to be close to an end of the first strap, and the guide pin 312 may be arranged to be relatively far away from the end of the first strap. In addition, the uniting tool 30 having one guide pin 312 and one catching pin 314 according to various embodiments of the present disclosure more facilitates a motion of wearing on the wrist, than a uniting tool having only one catching pin.

The guide pin 312 and the catching pin 314 may be configured to have roughly cylindrical shapes, respectively, but may be configured to have a multi-sided pillar shape. The multi-sided pillar shape includes a shape such as a four-angle pillar, a five-angle pillar, a six-angle pillar and the like.

The guide pin 312 is bound to the first strap and is inserted into a wearing hole 221 (shown in FIG. 2 or 4) of the second strap, thereby preventing the floating of the first and second straps, together with the catching pin 314. In other words, when the first and second straps are bound to the wrist, the guide pin 312 is selectively inserted into the wearing hole 221 of the second strap and primarily guides a wearing action. If the catching pin 314 is coupled to the wearing hole 221 of the second strap, the guide pin 312 prevents the floating of the first and second straps, together with the catching pin 314.

A construction of the wearable device according to various embodiments of the present disclosure is described below with reference to FIGS. 11 to 20.

Figure 11:
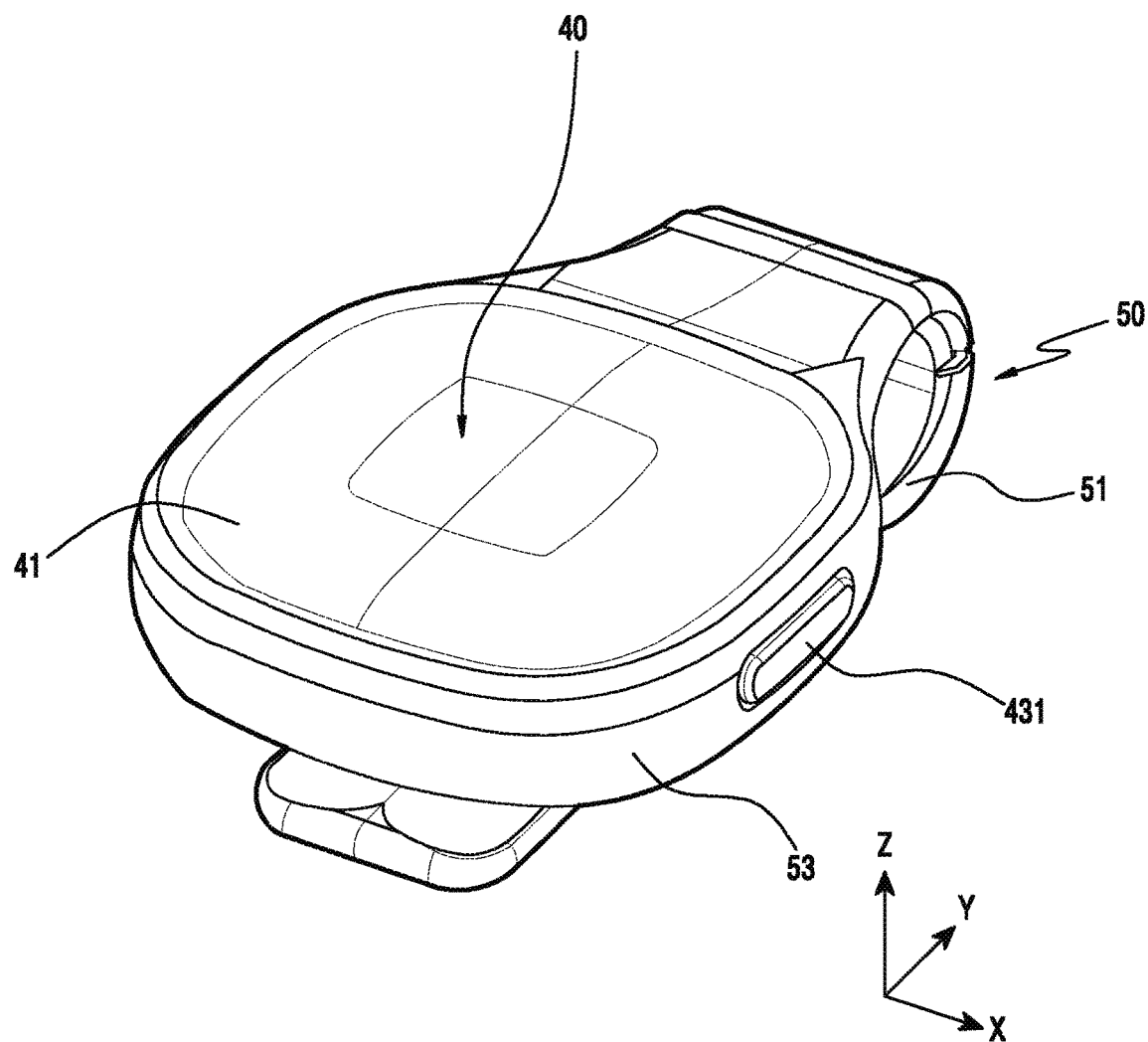
FIGS. 11 and 12 are perspective diagrams illustrating a wearable device coupling a body and a clip type wearing part according to various embodiments of the present disclosure.
Figure 12:
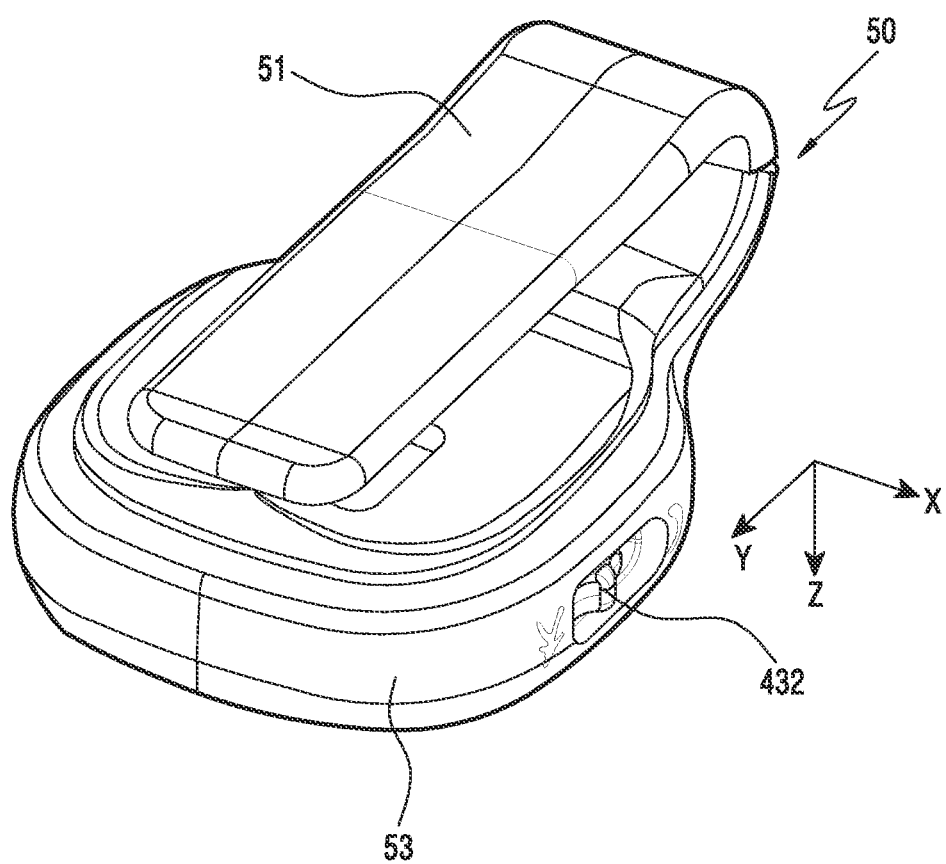

FIGS. 11 and 12 are perspective diagrams illustrating a wearable device coupling a body and a clip type wearing part according to various embodiments of the present disclosure.

Figure 13:
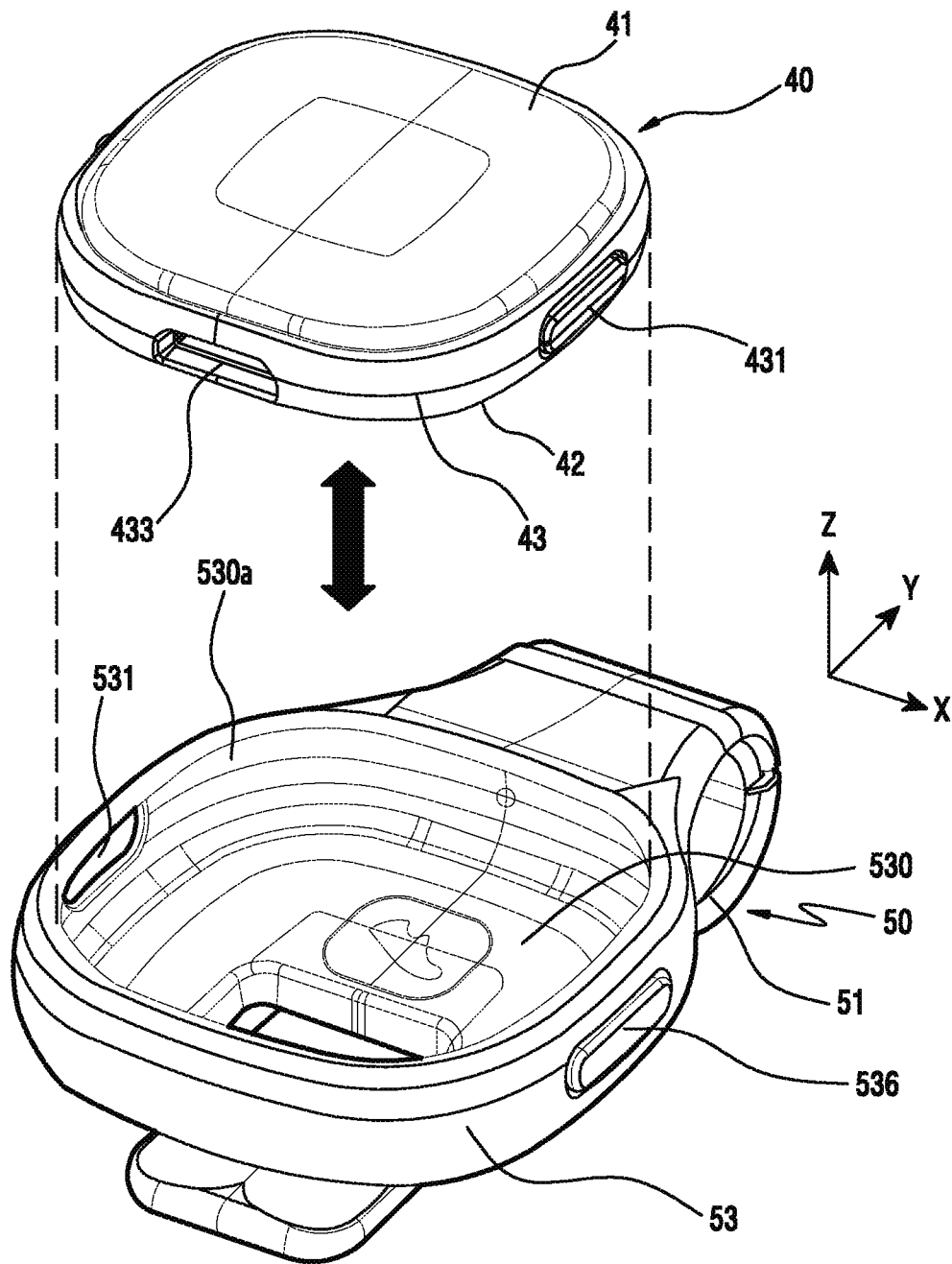
FIG. 13 is a perspective diagram illustrating a wearable device separating a body and a clip type wearing part according to various embodiments of the present disclosure.

FIG. 13 is a perspective diagram illustrating a wearable device separating a body and a clip type wearing part according to various embodiments of the present disclosure.

Referring to FIGS. 11 to 13, three-dimensional X/Y/Z rectangular coordinate systems are shown in the respective figures. 'Z axis' is vertical orientation and represents up/down orientation (i.e., thickness orientation) of a body 40. 'X axis' is first horizontal orientation and represents horizontal orientation of the body 40. 'Y axis' is second horizontal orientation being vertical to the first horizontal orientation and represents vertical orientation of the body 40.

The wearable device according to various embodiments of the present disclosure is an electronic device or communication device capable of being mounted on clothes or other articles and, for instance, is a device convenient for wearing on a coat, pants, a hat worn on the human body, or the like. In addition, it should be noted that, if a wearing part 50 is constructed variously, the wearable device according to the various embodiments of the present disclosure may be stably worn on various portions of the human body, or be worn on clothes of the human body or articles carried by users. The wearable device according to various embodiments of the present disclosure may include a body 40 (i.e., a function device part), and a clip type wearing part 50. The body 40 may be configured to be forcedly fitted to or separable from the clip type wearing part 50.

The body 40 according to the various embodiments of the present disclosure may include a key for inputting various kinds of information, a sensor, an interface part, and/or a component for notification occurrence. Additionally, the body 40 may arrange a display for displaying various information, a touch input part, a vibration element, and the like. The body 40 may have a roughly square appearance having a given thickness. However, the body 40 is not limited to a shape of the roughly square appearance, and may make various shape modifications. For instance, the body 40 may be configured to have a curved surface as well as a flat surface as an upper surface. The curved surface may be configured to have a curvature. In addition, the body 40 may be modified and embodied in a circle, oval, or long bar type. Because the body 400 takes charge of a function of a housing forming an appearance, the body 40 and the housing may be stated in combination.

The clip type wearing part 50 according to various embodiments of the present disclosure may be configured to have elasticity and make attachment and detachment of the body 40 possible, and may make it possible to stably wear the body 40 on clothes or other articles. In addition, because the clip type wearing part 50 is changeable, the clip type wearing part 50 takes charge of a function of an accessory exhibiting user's individuality or taste. However, a portion 53 (i.e., safe mounting part) of the clip type wearing part 50 coupled to the body 40 may be configured to make elastic deformation possible, and a clip part 51 may be formed of elastic materials such that the clip part 51 may be attached to and detached from clothes, or may be formed of two or more materials, or may have elasticity but not be formed of elastic materials, for instance, may be formed of metal materials. The body 40 may further include one or a plurality of keys 431 and 432 and an interface part connector 433.

The clip type wearing part 50 may include a first opening 530, a safe mounting part 53 being of a shape of covering a circumference of the first opening 530 and elastically deformed, and the clip part 51 constructed integrally with or independently of the safe mounting part 53 for assembly. The clip type wearing part 50 may include the safe mounting part 53 provided at least along the circumference of the first opening 530. The clip type wearing part 50 may include a part for allowing at least a portion of the safe mounting part 53 to be closely adhered to at least a portion of the body 40 when the body 40 is coupled to the clip type wearing part 50. In addition, the clip type wearing part 50 may be formed of one or a plurality of materials. That is, the safe mounting part 53 and the clip part 51 may be formed of different materials. The clip part 51 may be formed of two or more materials. The aforementioned two or more materials may include metal materials and synthetic resin materials. The synthetic resin materials may be any one of rubber, silicon, and urethane, or a combination of them.

The first opening 530 according to various embodiments of the present disclosure is a recess for coupling the body 40, and is of a shape in which a circumference and bottom of the first opening 530 are surrounded by the safe mounting part 53. The first opening 530 according to the present embodiment of the present disclosure may be configured to have a roughly square shape having a thickness. In addition, the safe mounting part 53 may have an additional opening 531. The additional opening 531 may be an opening for exposing a key (shown in FIG. 12) to the exterior of the safe mounting part 53. In addition, the body 40 may be configured to have a roughly square shape slightly bigger than the first opening 530 of the safe mounting part 53.

In addition, the wearable device according to an embodiment of the present disclosure includes a detachable structure in which the body 40 is coupled and separated mechanically from the clip type wearing part 50. The detachable structure of the wearable device may be implemented by coupling of an appearance shape of the body 40 and a shape of the first opening 530, materials of the safe mounting part 53, a separate coupling structure and the like. The first opening 530 of the safe mounting part 53 is configured to have a size (i.e., horizontal, vertical, and thickness sizes) slightly smaller than the body 40. Thus, if the body 40 is forcedly coupled to the first opening 530 of the safe mounting part 53, the body 40 may be tightly fitted to the safe mounting part 53. The safe mounting part 53 is elastically deformed and the first opening 530 is configured to have a volume of coupling or separating the body 40 by a forced user's force, thereby making possible an attachment and detachment operation of the body 40. Specifically, the safe mounting part 53 is of a shape of having an inner wall 530a capable of adhering to, specifically, covering a circumference of the body 40. If the body 40 is coupled to the safe mounting part 53, the body 40 is not separated from the safe mounting part 53 by means of friction generated by an adherence surface between the body 40 and the safe mounting part 53, as long as an external force is not forcedly applied for separation.

In addition, the body 40 may be forcedly fitted or separable with directivity from the safe mounting part 53, by means of a shape of the body 40 and a structure of the safe mounting part 53. The safe mounting part 53 may be configured to have a shape of covering the whole side circumference of the body 40 and a bottom surface thereof. At least the portion of the bottom surface of the safe mounting part 53 may be configured to be opened and have a second opening (shown in FIG. 16).

Although described below in detail, the body 40 may include a front case 41, a rear case 42, and a connection case 43. The connection case 43 is configured to have a size of gradually decreasing vertical and horizontal widths as it goes to upper and lower ends starting from a middle portion. The inner wall 530a of the safe mounting part 53 is tightly closely adhered to the connection case 43 of the body 40, whereby the body 40 may be stably coupled to the safe mounting part 53 by means of a friction force between the inner wall 530*a* and the connection case 43. The cases is described in detail later.

Because the clip type wearing part 50 according to various embodiments of the present disclosure has a changeable structure, the clip type wearing part 50 is changeable anytime according to user's tastes if being implemented in various designs and colors. Reference numeral 536 denotes a key press part for pressing the first side key 431 of the body 40 when the body 40 is coupled to the safe mounting part 53.

Figure 14:
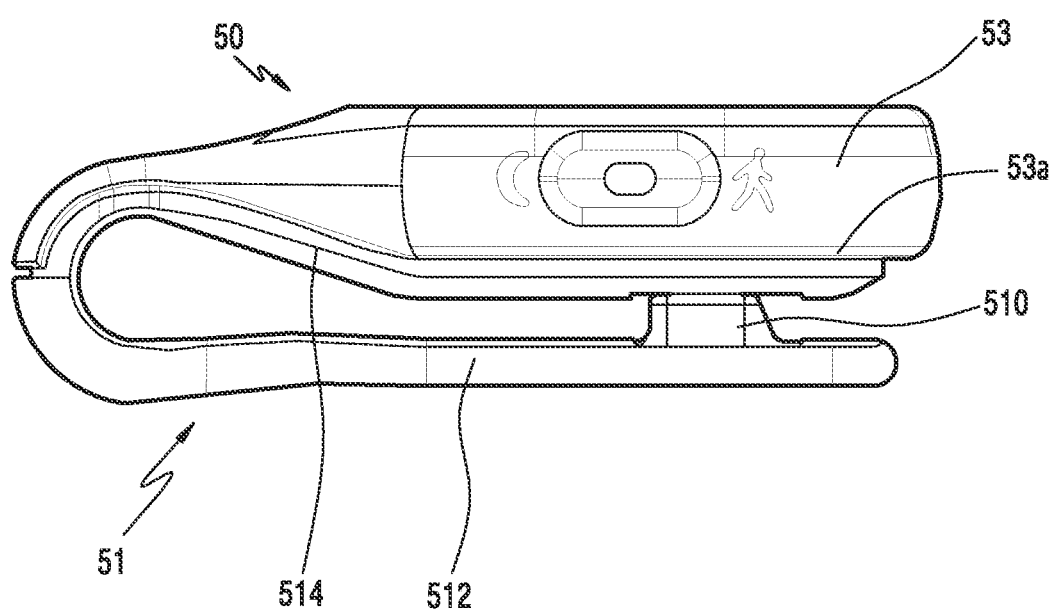
FIG. 14 is a side diagram illustrating a wearable device according to various embodiments of the present disclosure.

FIG. 14 is a side diagram illustrating a wearable device according to various embodiments of the present disclosure.

Figure 15:
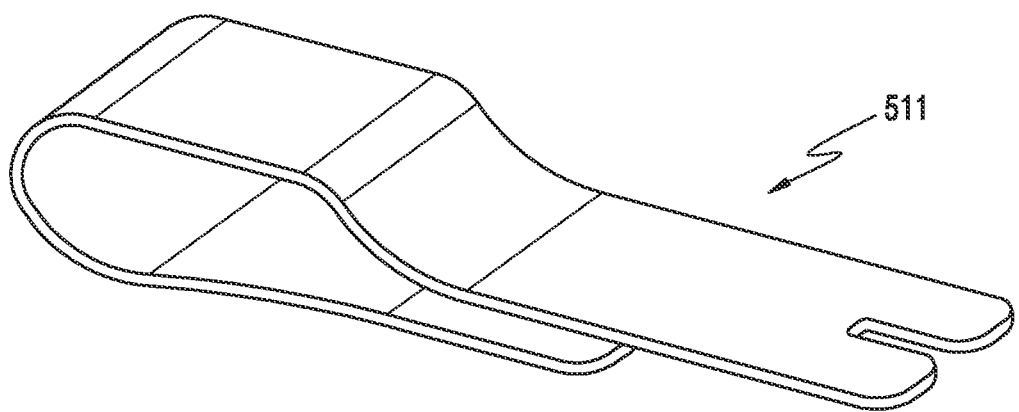
FIG. 15 is a perspective diagram illustrating a clip provided in a clip part according to various embodiments of the present disclosure.

FIG. 15 is a perspective diagram illustrating a clip provided in a clip part according to various embodiments of the present disclosure.

Referring to FIGS. 14 and 15, a clip type wearing part 50 may include a clip part 51 extended and bent from the safe mounting part 53, and providing a force closely adhering to a bottom portion 53*a* of the safe mounting part 53. The clip part 51 is extended from the safe mounting part 53 in one orientation (i.e., Y-axis orientation), and is again extended to the bottom portion 53*a* of the safe mounting part 53 in opposite orientation of the extension orientation. In addition, the clip part 51 may be configured to hold an elastic force of getting an end of the clip part 51 close to the bottom portion 53*a* of the safe mounting part 53.

The end region of the clip part 51 may have a structure of tightly adhering to the bottom portion 53*a* of the safe mounting part 53. The end region of the clip part 51 may be implemented to have a structure overlapping with a portion of the bottom portion 53*a* of the safe mounting part 53.

The clip part 51 may be formed of materials different from those of the safe mounting part 53. The clip part 51 may be formed of two or more materials. The safe mounting part 53 may be formed of soft urethane or silicon materials. On the other hand, the clip part 51 may be formed of stiff polycarbonate (PC) materials, or may be configured to have a clip type metal fragment 511 applied to the whole section or partial section of the clip part 51. The clip type metal fragment 511 is illustrated in FIG. 15. Because the clip part 51 is formed of stiffer materials than the safe mounting part 53, the clip part 51 may have elasticity for preventing the clip part 51 from being separated when a user wears the wearable device on clothes or in other positions. In addition, the clip part 51 may be configured to cover rigid materials 514 with soft materials 512 in at least a partial section of the clip part 51.

The clip part 51 may further include a rib 510 formed at an end of the clip part 51 and overlapped with the bottom portion 53*a* of the safe mounting part 53. The rib 510 is protruded from the end of the clip part 51 toward the bottom portion 53*a* of the safe mounting part 53, and is extended to have a length of the extent of overlapping with the bottom portion 53*a* or overlapping with a part of an opening region provided in the bottom portion 53*a*.

Figure 16:
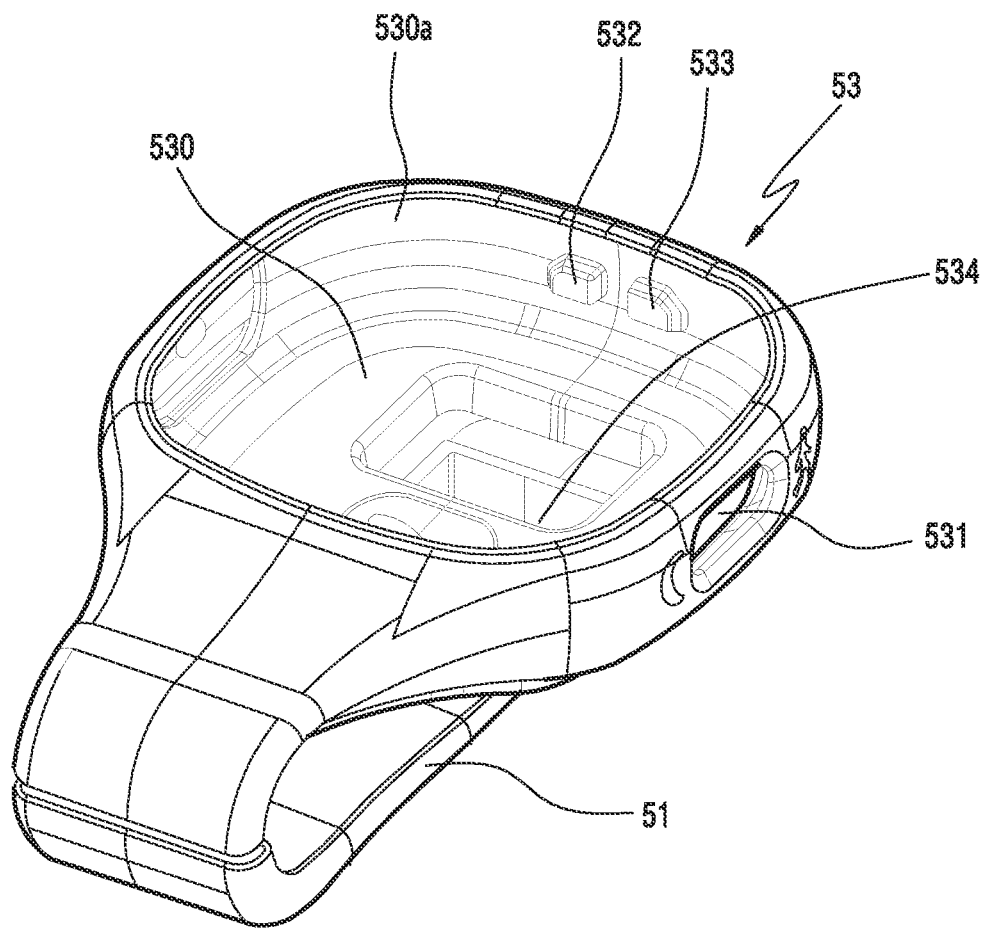
FIG. 16 is a perspective diagram illustrating a construction of a safe mounting part according to various embodiments of the present disclosure.

FIG. 16 is a perspective diagram illustrating a construction of a safe mounting part according to various embodiments of the present disclosure.

Figure 17:
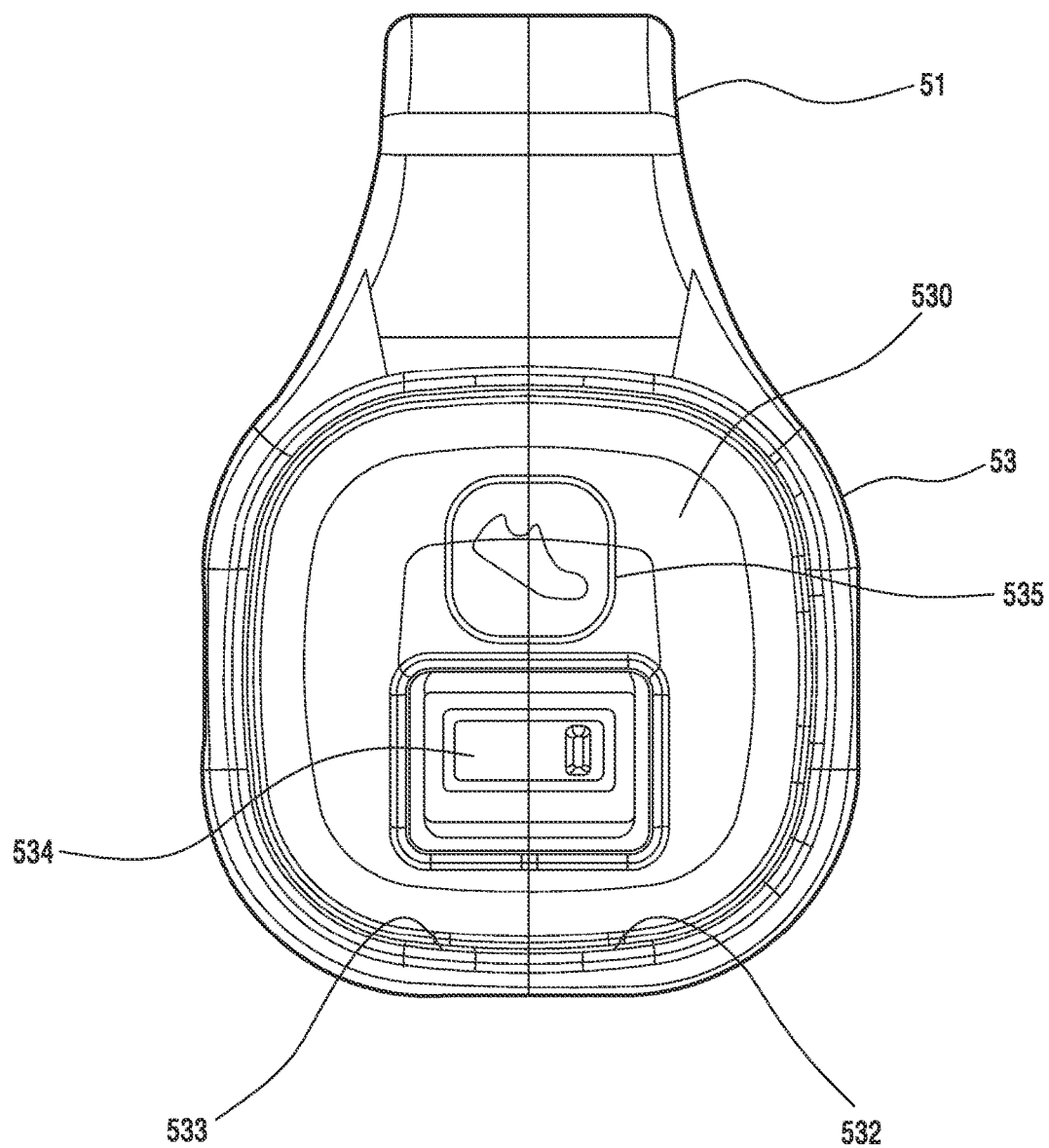
FIG. 17 is a plane diagram illustrating a construction of a safe mounting part according to various embodiments of the present disclosure.

FIG. 17 is a plane diagram illustrating a construction of a safe mounting part according to various embodiments of the present disclosure.

Figure 18:
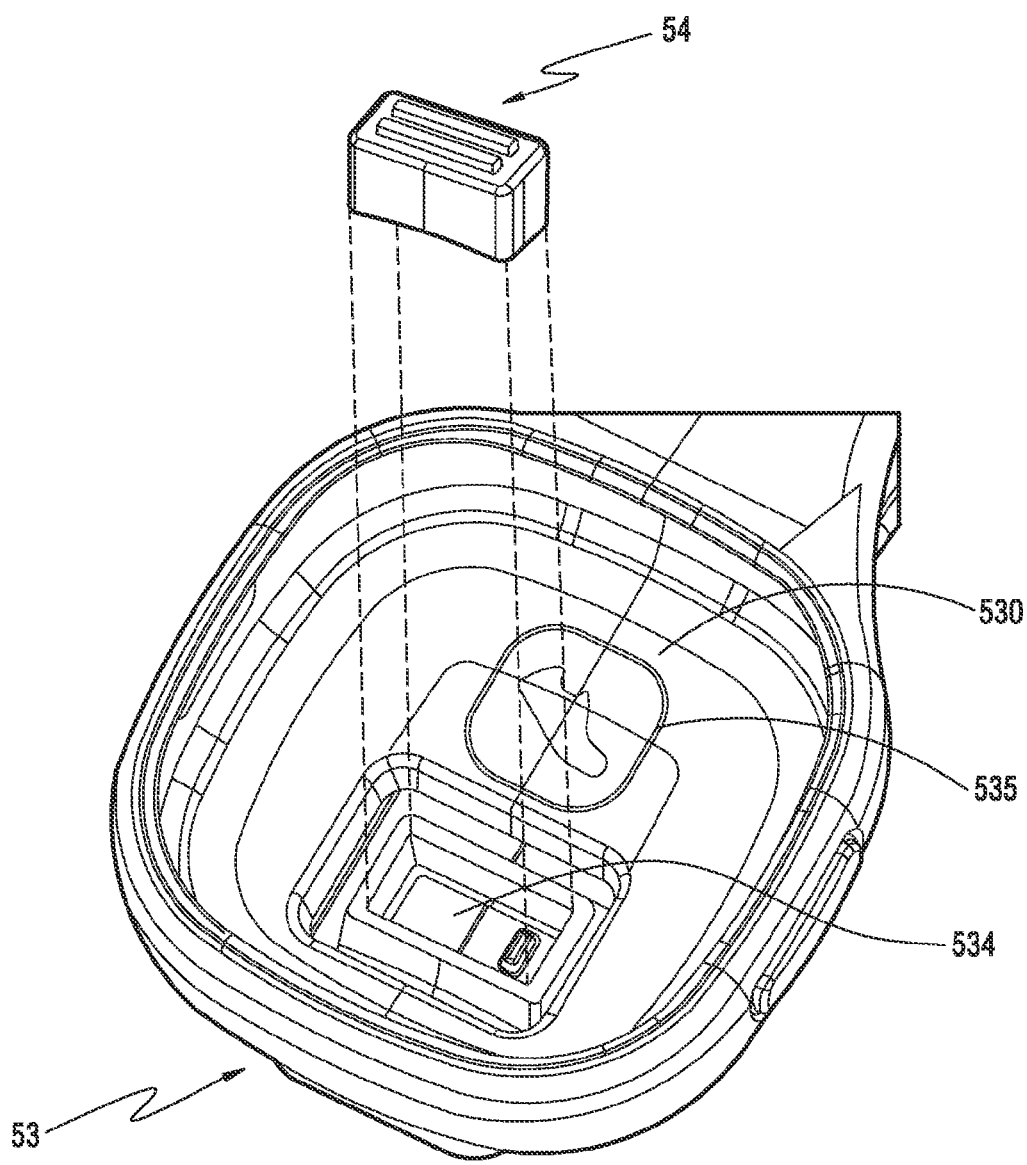
FIG. 18 is a perspective diagram illustrating a state of inserting an anti-sliding member into a safe mounting part according to various embodiments of the present disclosure.

FIG. 18 is a perspective diagram illustrating a state of inserting an anti-sliding member into a safe mounting part according to various embodiments of the present disclosure.

Referring to FIGS. 16 to 18, a part of a safe mounting part 53 and a clip part 51 may be integrally constructed through PC injection according to various embodiments of the present disclosure. In this case, the safe mounting part 53 may have a second opening 534 corresponding to a position and shape of the rib 510 of the clip part 51 so as to install the rib 510 in a partial section of the clip part 51, for instance, in the end of the clip part 51. This second opening 534 is essential to formation of the rib 510, in view of injection molding. After the rib 510 is partially overlapped inside the second opening 534, the rib 510 is deformed and completed by heat molding after the first injection molding.

In addition, the safe mounting part 53 is configured to provide the second opening 534 in the bottom portion 53*a* of the safe mounting part 53, thereby being capable of housing the rib 510 in the four-side clogged second opening 534. A structure of the second opening 534 may further provide an assembly structure having additional components such as an anti-sliding rubber 54 and the like. If the anti-sliding rubber 54 is inserted into the second opening 534, the rib 510 housed in the second opening 534 may be closely adhered to the anti-sliding rubber 54 inserted into the second opening 534.

One or a plurality of coupling parts 532 and 533 (e.g., coupling protrusions) capable of coupling with various interface part connectors may be provided in the inner wall 530*a* of the safe mounting part 53 such that, when the body is mounted, the body may be prevented from being inversely inserted and being rotated in a mounting state. Particularly, the coupling parts 532 and 533 may be provided in plural.

Additionally, the same recognition icon 535 is engraved on the body and a bottom of the safe mounting part 53 such that coupling directivity may be prejudged by a user when the body is initially inserted.

Figure 19A:
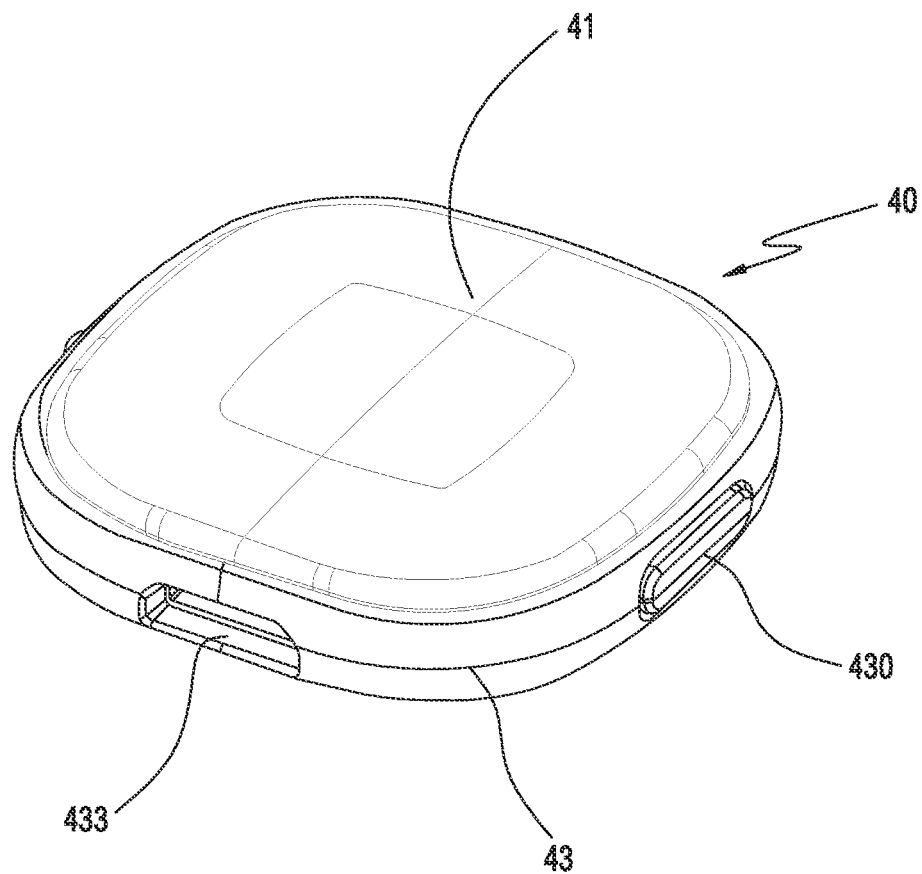
FIGS. 19A and 19B are perspective diagrams illustrating states viewing a body in different orientations respectively according to various embodiments of the present disclosure.
Figure 19B:
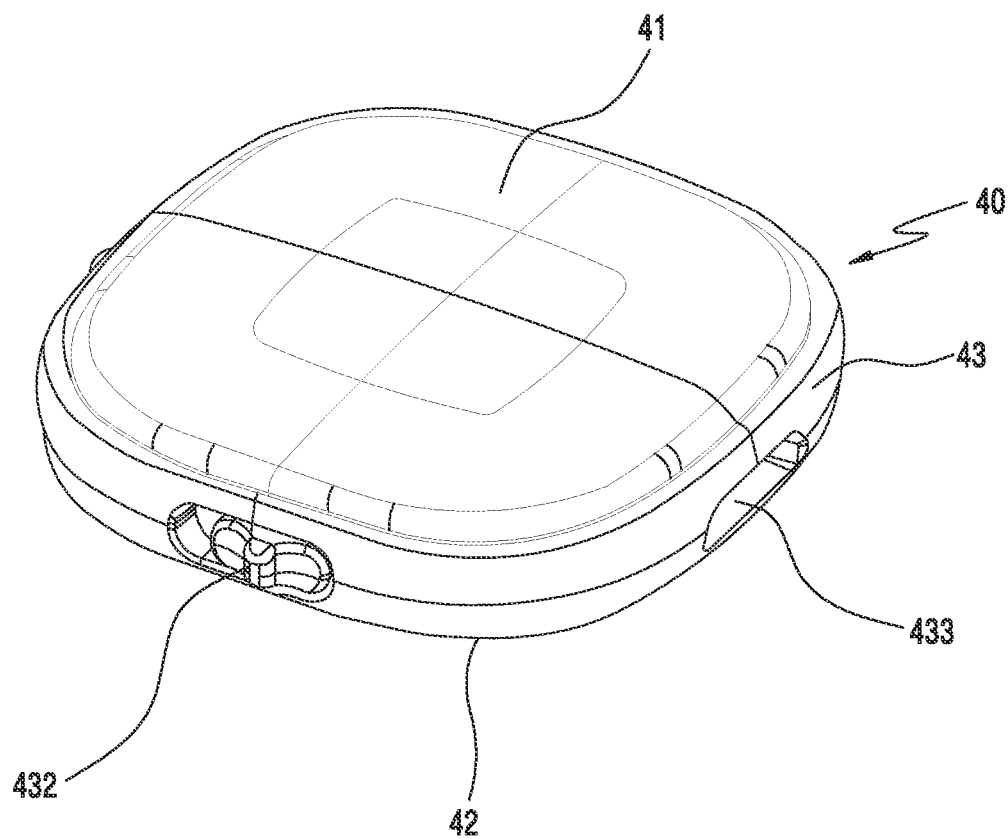

FIGS. 19A and 19B are perspective diagrams illustrating states viewing in different orientations a body respectively according to various embodiments of the present disclosure.

Referring to FIGS. 19A and 19B, the body 40 according to various embodiments of the present disclosure may further include one or a plurality of keys for inputting various information, an input/output terminal part enabling data input/output, a touch input part not shown, a display part, and the like. In addition, the body 40 may include a boozer for signal generation, LEDs, various switches, a terminal part and the like, inclusive of various processors, a memory, an antenna, a battery and the like which are basically included in a mobile device. Additionally, the body 40 may further include a vibrator not shown, a speaker, a receiver, a camera, a flash, a memory slot, and the like.

In addition, the body 40 according to various embodiments of the present disclosure may consist of three cases 41, 42, and 43. The three cases 41, 42, and 43 may be coupled with one another and take charge of a function and appearance of a housing of the body 40. Referring to FIG. 7, the body 40 may include the front case 41, the connection case 43, and the rear case 42 which are shown to a user when the body 40 is coupled to the wearing part. The front case 41 may arrange a display, and may be constructed as a transparent or semitransparent case. In addition, the front case 41 may be configured to have a curvature, or to not have the curvature. If the front case 41 has the curvature, the front case 41 may be a curved display. If the front case 41 does not have the curvature, the front case 41 may be a flat display. The display may include a touch screen, an LCD, an OLED, and the like.

If the front case 41 is formed of transparent or semitransparent synthetic resins, light emitted from the internal of the body 40 becomes visible. Thus, a user may check the emitted light and recognize information meant by the light. Though described later, light emitted from an LED may be displayed through at least a portion of the front case 41. In this case, at least the portion of the front case 41 may take charge of a function of light wave guide.

The connection case 43 represents a lateral surface of the body 40, and may physically include one or a plurality of keys 430 and 432. FIG. 19A illustrates one example of arranging the first side key 430 operated by a user's physical press motion, and FIG. 19B illustrates one example of arranging the second side key 432 (i.e., slide key) configured to face the first side key 430. The connection case 43 is configured to have a curved surface which is slightly convexed outwards. Thus, when the body 40 is fully coupled to the safe mounting part, the connection case 43 of the body 40 gives help for prevention of separation of the body 40. An interface part connector 433 may be arranged in a circumference surface between the first and second side keys 430 and 432.

The front case 41 of the body 40 may be configured to have a curved surface as well as a flat surface. The curved surface may be configured to have a curvature. In addition, the body 40 may be modified and embodied in a circle, oval, or long bar type. Additionally, the front case 43 of the body 40 may arrange a display including an LCD or OLED, and may have a touch screen inputting/outputting various information.

To implement an ultralight and low power device, a subminiature wearable device according to various embodiments of the present disclosure may remove various output devices of general electronic devices, or have substitutes for them. A visual output device such as the existing LCD and OLED displays may be replaced with LEDs, and a sound and tactile output device such as a speaker and a vibrator may be also replaced with a boozer.

The present embodiment of the present disclosure includes an invisible LED mounting structure (described later) in a rear surface of the front case 41 such that a user cannot recognize the existence of LEDs (shown in FIG. 29) or light emitting parts by appearances when the LEDs are in an Off state. The front case 41 is formed through semitransparent injection. A micro silver layer may be coated on the front case 41 at a suitable thickness such that light may be emitted out passing through an injection surface when the LEDs turn on.

This may be replaced with painting, deposition, plating, and the like not disclosed in the present disclosure. A fine pattern of a hairline form may be formed in an injection surface. In addition, the LEDs may be arranged in an appearance section being an almost flat surface. A flat safe mounting structure may be provided in an inner surface of the front case 41 facing the LEDs, and prevent the deflection and leakage of light traveling from the LEDs.

Figure 20A:
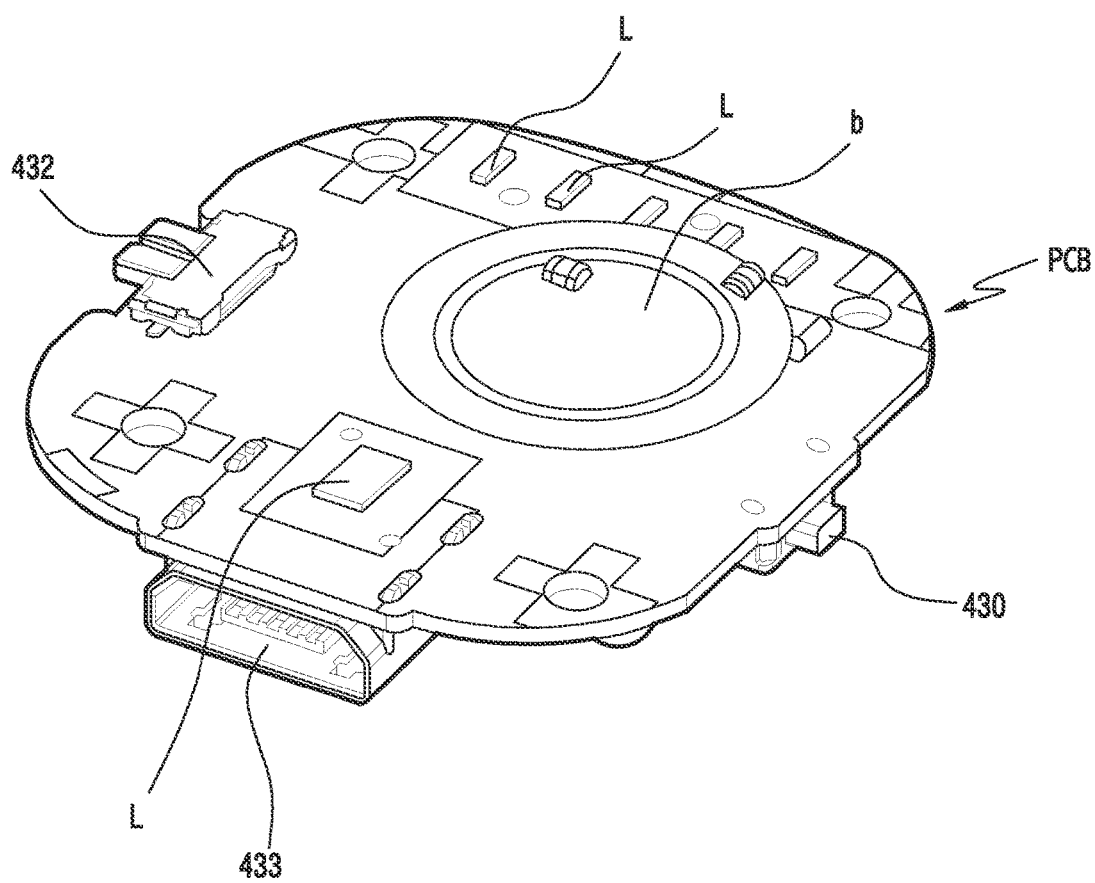
FIG. 20A is a perspective diagram illustrating components mounted in one surface of a Printed Circuit Board (PCB) within a body according to various embodiments of the present disclosure.

FIG. 20A is a perspective diagram illustrating components mounted in one surface of a Printed Circuit Board (PCB) within a body according to various embodiments of the present disclosure.

Figure 20B:
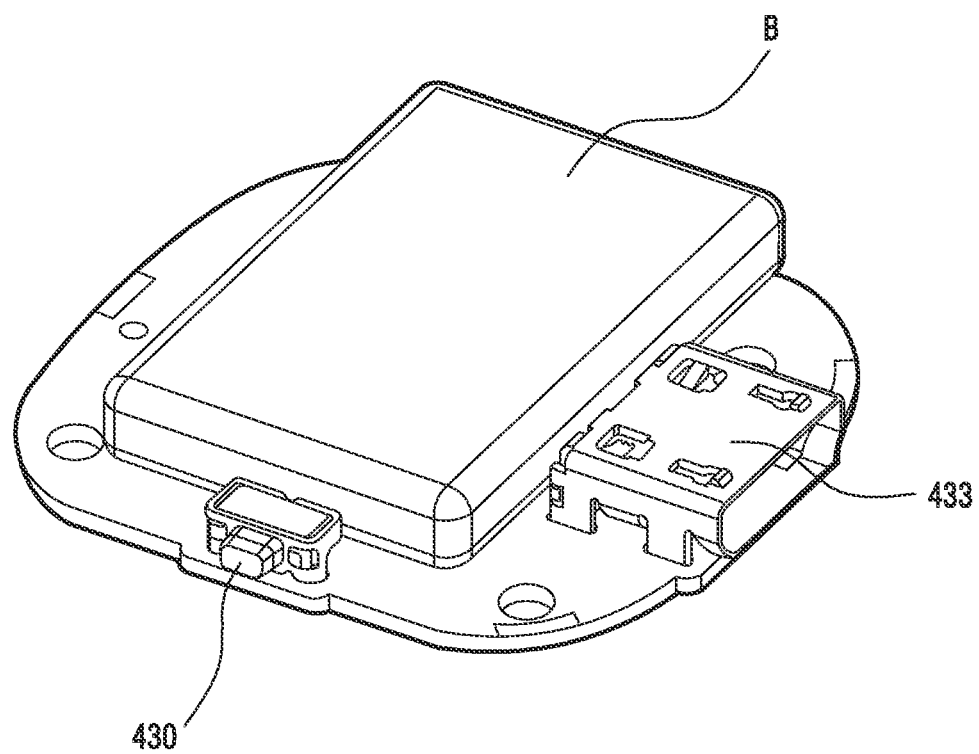
FIG. 20B is a perspective diagram illustrating components mounted in the other surface of a PCB within a body according to various embodiments of the present disclosure.

FIG. 20B is a perspective diagram illustrating components mounted in another surface of the PCB within a body according to various embodiments of the present disclosure.

Referring to FIGS. 20A and 20B, a PCB installed within the body according to various embodiments of the present disclosure may mount various electronic components, input/output devices and the like for performing functions of the wearable device. As described earlier, the body is configured to have a three-piece structure (i.e., the front case, the connection case, and the rear case) for constructing the subminiature wearable device, and has a structure of coupling the three cases by ultrasonic fusion, thereby minimizing or removing a uniting structure for uniting the respective three cases.

A suitable electronic component mounting structure corresponding to this body structure is needed. Because of a characteristic of the ultrasonic fusion, components and products may suffer the deflection of compression. This may act as the cause of defects, such as deflection of performance of various contact type components, light leakage, waterproof, component and product damage, and the like. Considering this situation, in various embodiments of the present disclosure, elastic components or compressive components are mounted on one surface of the PCB such that the elastic components or compressive components face an inner surface of the front case pre-assembled (i.e., ultrasonic fusion) with the connection case, and are fixed to a PCB fixing hook of the connection case. By doing so, an unnecessary elastic force may be restrained in an assembly process, to prevent a deflection of product performance generated by a pushing force of the elastic components/compressive components in the final ultrasonic fusion step, and product damage by a pressurization of a mounting state.

The PCB arranged within the body 40 may arrange the second side key 432, a plurality of LEDs 435, and the like in one surface (i.e., an upper surface) of the PCB. The PCB may arrange the first side key 430, a battery (B), the interface part connector 433, and the like on the other surface (i.e., a bottom surface) of the PCB. The boozer 436 shown in FIG. 20A may be arranged in the front case.

Figure 21A:
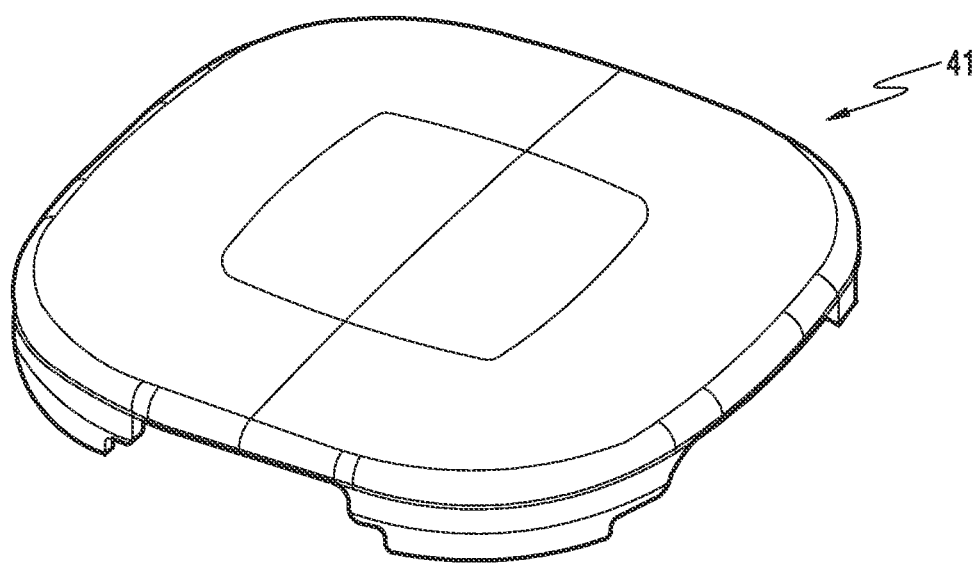
FIG. 21A is a perspective diagram illustrating a front case according to various embodiments of the present disclosure.

FIG. 21A is a perspective diagram illustrating a front case according to various embodiments of the present disclosure.

Figure 21B:
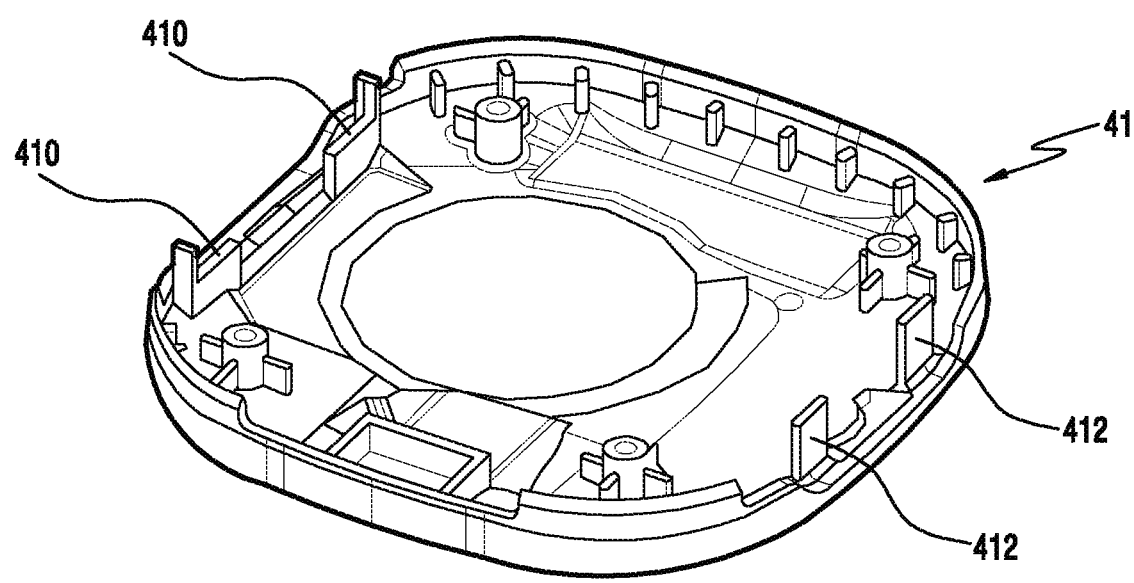
FIG. 21B is a perspective diagram illustrating an inner surface of a front case according to various embodiments of the present disclosure.

FIG. 21B is a perspective diagram illustrating an inner surface of the front case according to various embodiments of the present disclosure.

Figure 21C:
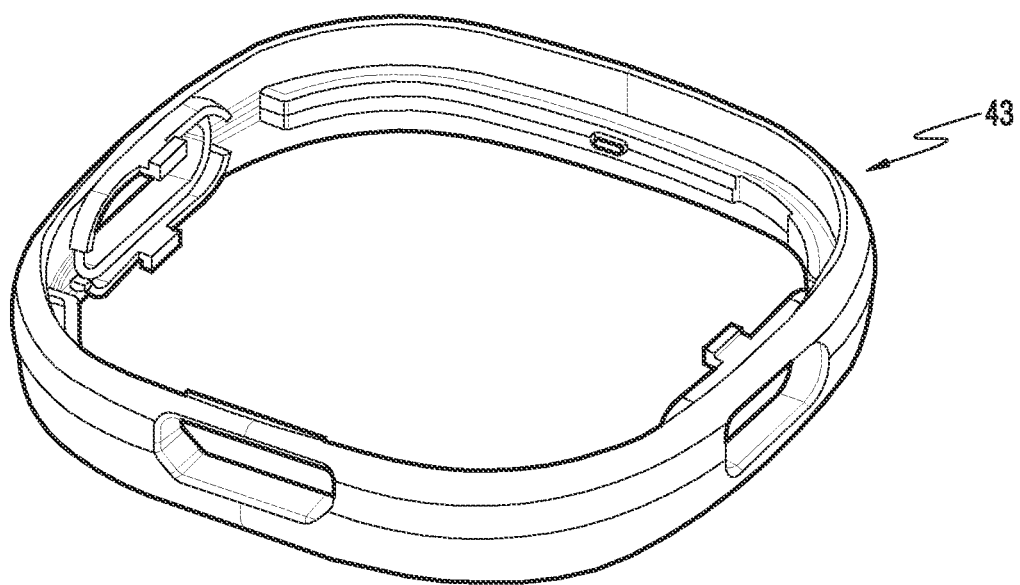
FIG. 21C is a perspective diagram illustrating a connection case according to various embodiments of the present disclosure.

FIG. 21C is a perspective diagram illustrating a connection case according to various embodiments of the present disclosure.

Figure 22:
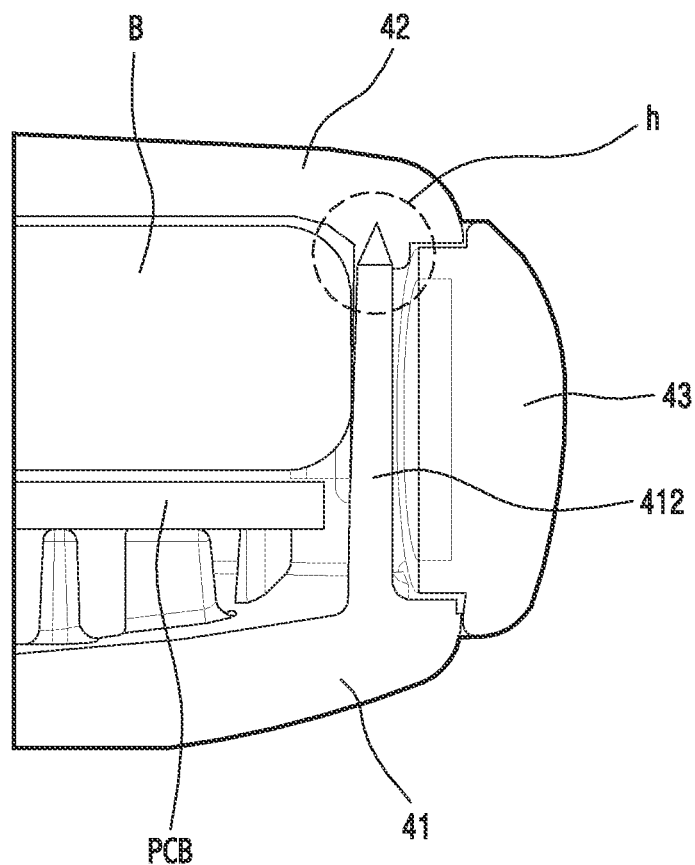
FIG. 22 is a cross section illustrating a coupling structure of body cases according to various embodiments of the present disclosure.

FIG. 22 is a cross section illustrating a coupling structure of body cases according to various embodiments of the present disclosure.

Referring to FIGS. 21A to 22, the housing of the body 40 according to various embodiments of the present disclosure consists of the front case 41, the connection case 43, and the rear case 42 as mentioned above. The respective cases 41, 42, and 43 are coupled with one another through ultrasonic heat fusion, thereby completing an appearance of the body 40. This coupling structure is very advantageous to a construction of the subminiature wearable device because being implemented by a structure capable of minimizing or removing various coupling structures for the sake of optimization of a component mounting space and implementation of a beautiful design.

The coupling structure of the cases 41, 42, and 43 according to the present disclosure may contribute to the slimming of the body 40 using an ultrasonic heat fusion method.

The front case 41 may have a plurality of first and second vertical walls 410 and 412 formed in regions where the first and second side keys are arranged. The first and second vertical walls 410 and 412 prevent separation of the first and second side keys. Though described later, the first and second vertical walls 410 and 412 may be used for coupling the cases 41, 42, and 43 through the ultrasonic heat fusion described later as well as preventing the separation of the first and second side keys.

Below, a description is made for a method of forming an appearance of the body using the ultrasonic heat fusion.

First, the front case 41 is coupled to the connection case 43 by ultrasonic fusion. For this, the first and second vertical walls 410 and 412 of the front case 41 are used as ultrasonic fusion ribs, respectively. And, an ultrasonic fusion safe mounting part (h), which is a counterpart assembly part, is provided in a lateral edge and rear cover of the connection case 43 of a generally ring shape. According to cases, it does not matter that the ultrasonic fusion rib and the counterpart assembly part (h) are substituted with each other in position. To secure required fusion strength, a length of the ultrasonic fusion rib compared to a set dimension may be changed. Specifically, the connection case 43 takes a roughly ring form, whereby various structures such as a side key safe mounting hole, a fixing structure, a PCB fixing hook part, and the like impossible to be formed within an injection molding stroke region or a processing tool dimension range in the existing two-piece assembly structure may be freely formed anywhere inside the connection case 43.

In addition, because the front case 41 may freely have a fixed assistant structure formed around a key assembly hole regardless of the key assembly hole, the front case 41 may save a key mounting and action space compared to the existing two-piece assembly structure, thereby contributing to the lightweighting and simplification of an electronic device set.

As described above, a three-piece housing structure according to various embodiments of the present disclosure safely mounts various electronic hardware components in the housing consisting of two kinds of the front case 41 and the connection case 43 and covers the housing with the rear case 42 to complete a set. Like the front case 41, the rear case 42 is provided through the ultrasonic fusion. Even a design specification of the rear case 42 is similar to that of the front case 41 described earlier. Particularly, in the structure in which the three-piece cases 41, 42, and 43 of the present embodiment of the present disclosure are coupled to one another through the ultrasonic fusion, the attachment strength of the finally assembled rear case 42 is an important factor controlling the robustness of an electronic device. In accordance to this, the ultrasonic fusion structure of connecting the rear case 42 and the connection case 43 is constructed similarly to the ultrasonic fusion structure of the front case 41. The ultrasonic fusion structure connecting the rear case 42 and the connection case 43 may additionally further have a strength reinforcement means.

An example of the strength reinforcement means is described. The front case 41 may increase heights of the first and second vertical walls (i.e., the ribs for prevention of key separation) and be connected by ultrasonic fusion with an inner side of the rear case 42 assembled after PCB mounting, thereby increasing the robustness of the set around a key installation part being generally weak. Undoubtedly, even the contrary case is possible, and various modifications (e.g., a pole structure and the like) are possible beside the illustrated rib form.

Figure 23A:
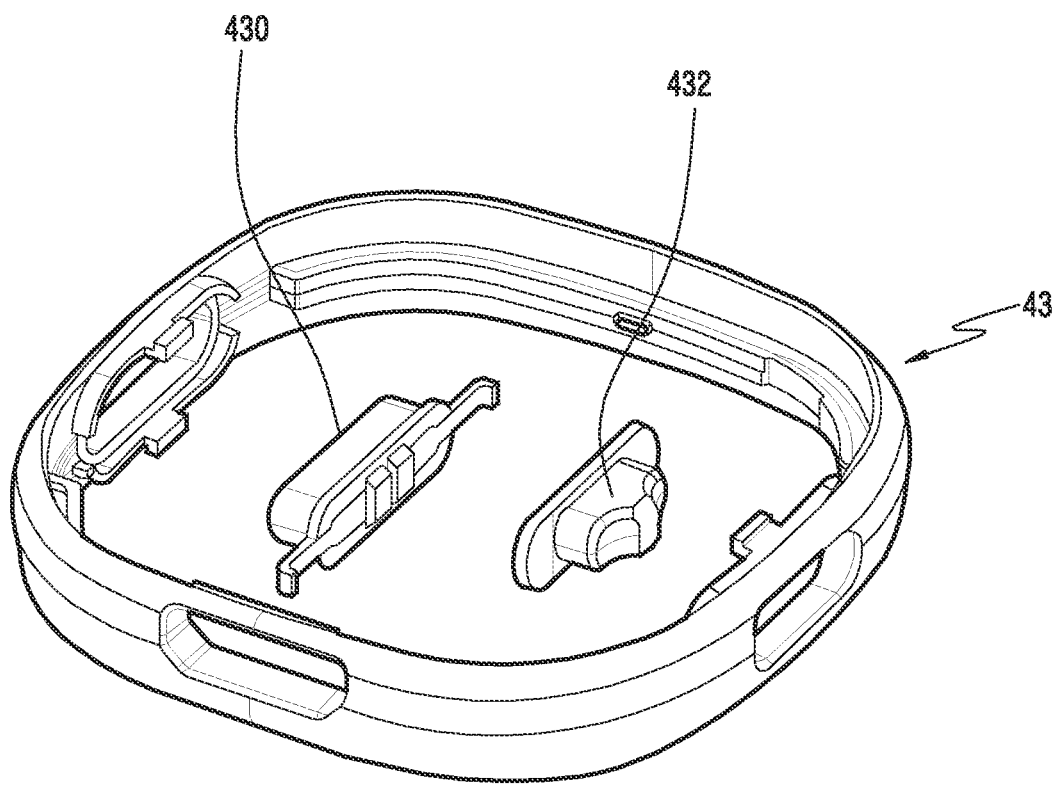
FIG. 23A is a perspective diagram illustrating a state of assembling first and second side keys to a connection case according to various embodiments of the present disclosure.

FIG. 23A is a perspective diagram illustrating a state of assembling first and second side keys to a connection case according to various embodiments of the present disclosure.

Figure 23B:
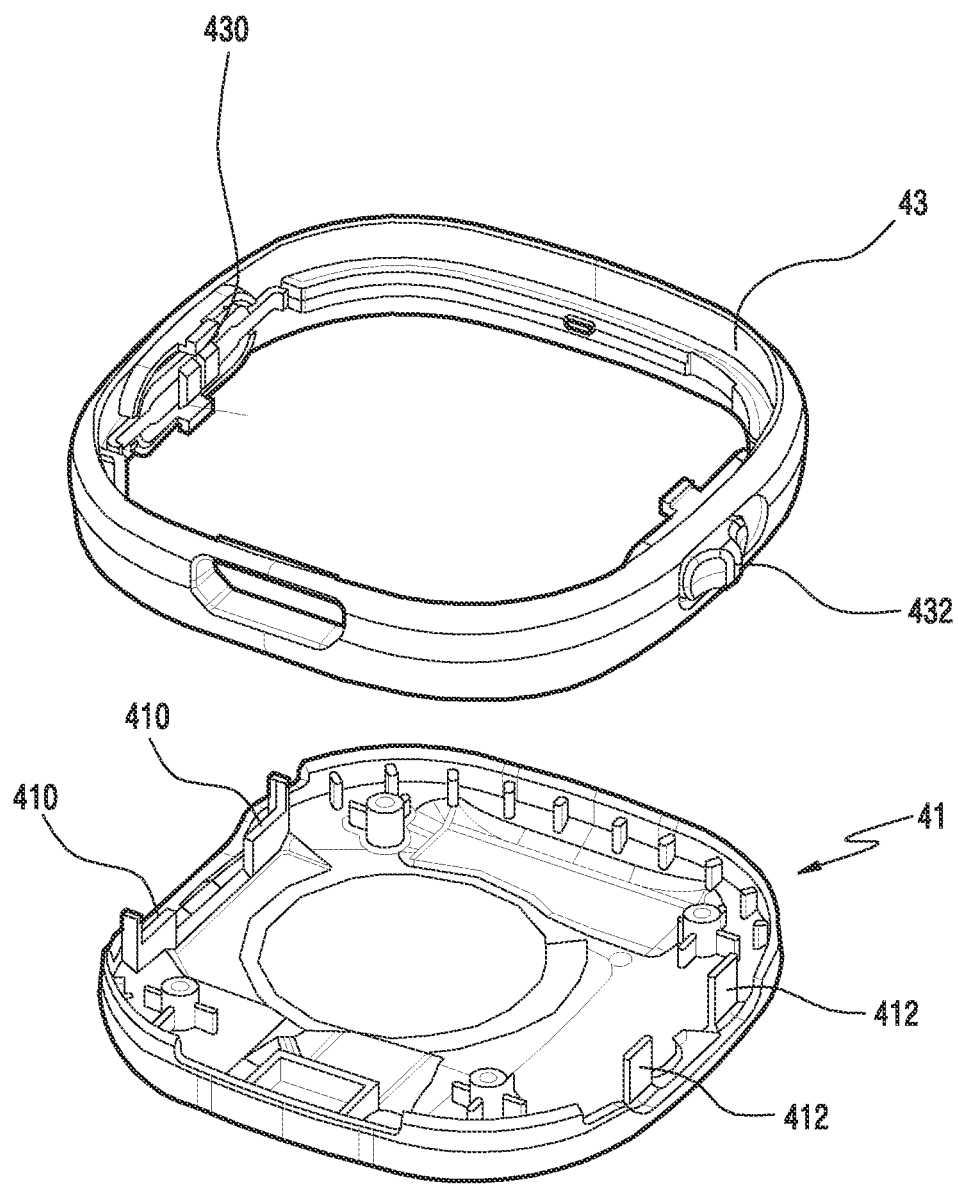
FIG. 23B is a perspective diagram illustrating a state of before assembling a front case with a connection case assembled with first and second keys according to various embodiments of the present disclosure.

FIG. 23B is a perspective diagram illustrating a state of before assembling a front case with the connection case assembled with first and second keys according to various embodiments of the present disclosure.

Figure 23C:
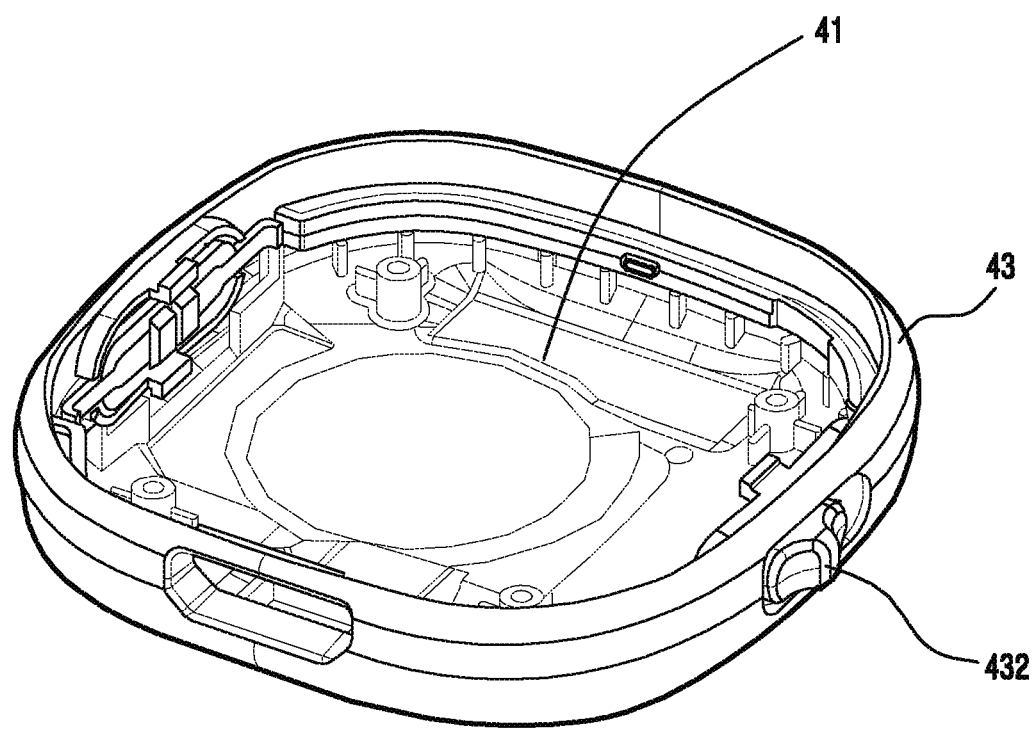
FIG. 23C is a perspective diagram illustrating a state of coupling a front case with a connection case according to various embodiments of the present disclosure.

FIG. 23C is a perspective diagram illustrating a state of coupling a front case with a connection case according to various embodiments of the present disclosure.

Referring to FIGS. 23A to 23C, the order of body assembly is described. A body assembly method according to various embodiments of the present disclosure assembles various keys (e.g., the first side key 430 and the second side key 432) to key holes of the connection case 43 forming a portion of a body appearance respectively (shown in FIG. 22B) and then, safely mounts in the connection case 43 the front case 41 forming a portion of the body appearance and then, performs ultrasonic fusion at a boundary between the front case 41 and the connection case 43. At this time, a key floating prevention structure (e.g., the first and second vertical walls 410 and 412) is separately provided in the front case 41 and prevents key separation and floating upon assembly compared to the existing two-piece structure. This may improve the accuracy of an operation and the quality of an appearance.

This structure design method may greatly contribute to the lightweighting and simplification of the subminiature wearable device as in the present embodiment of the present disclosure even without using a separate piece, by freely providing a key in a desired position by suitably distributing the proximal arrangement of a key hole 430a and the key floating prevention structure, which were impossible to be implemented for the reasons of molding and processing in the existing two-piece assembly type electronic device structure, to the front case 41 and connection case 43.

Figure 24A:
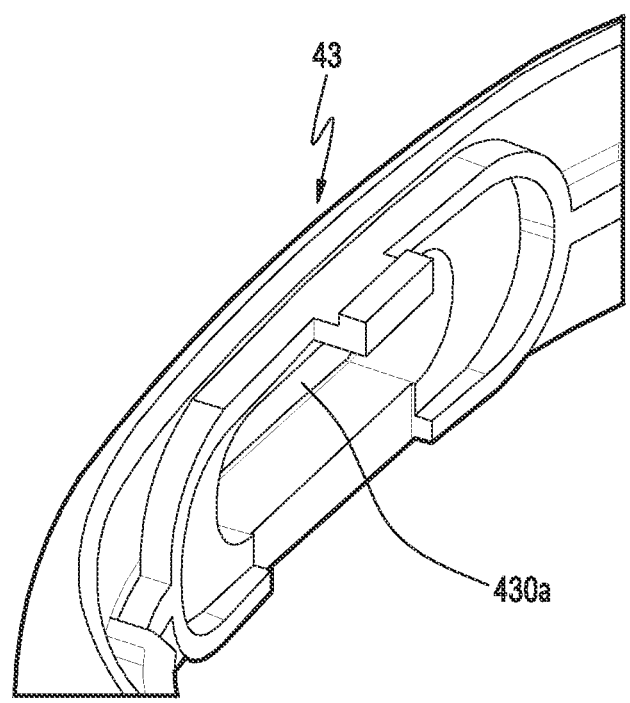
FIG. 24A is a perspective diagram illustrating a coupling structure of a second side key provided in a connection case according to various embodiments of the present disclosure.
Figure 24B:
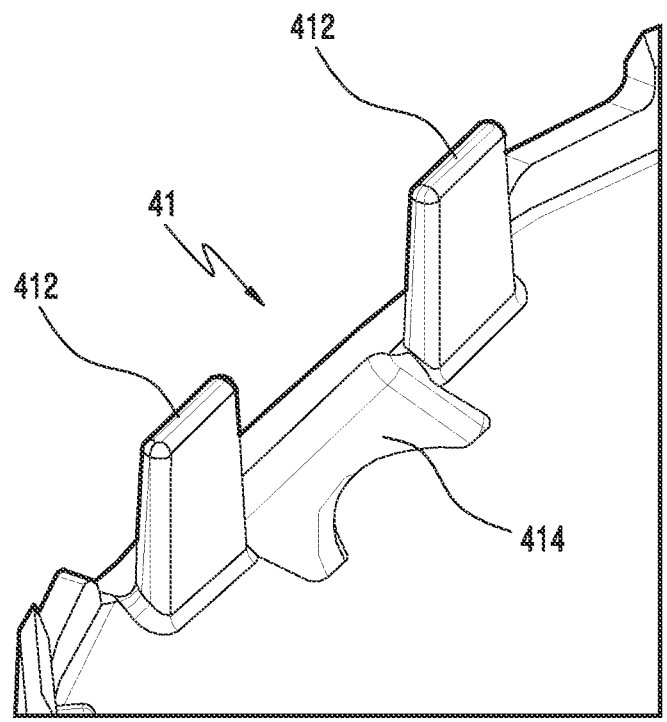
FIG. 24B is a perspective diagram illustrating a vertical wall and a recess provided in a front case according to various embodiments of the present disclosure.
Figure 24C:
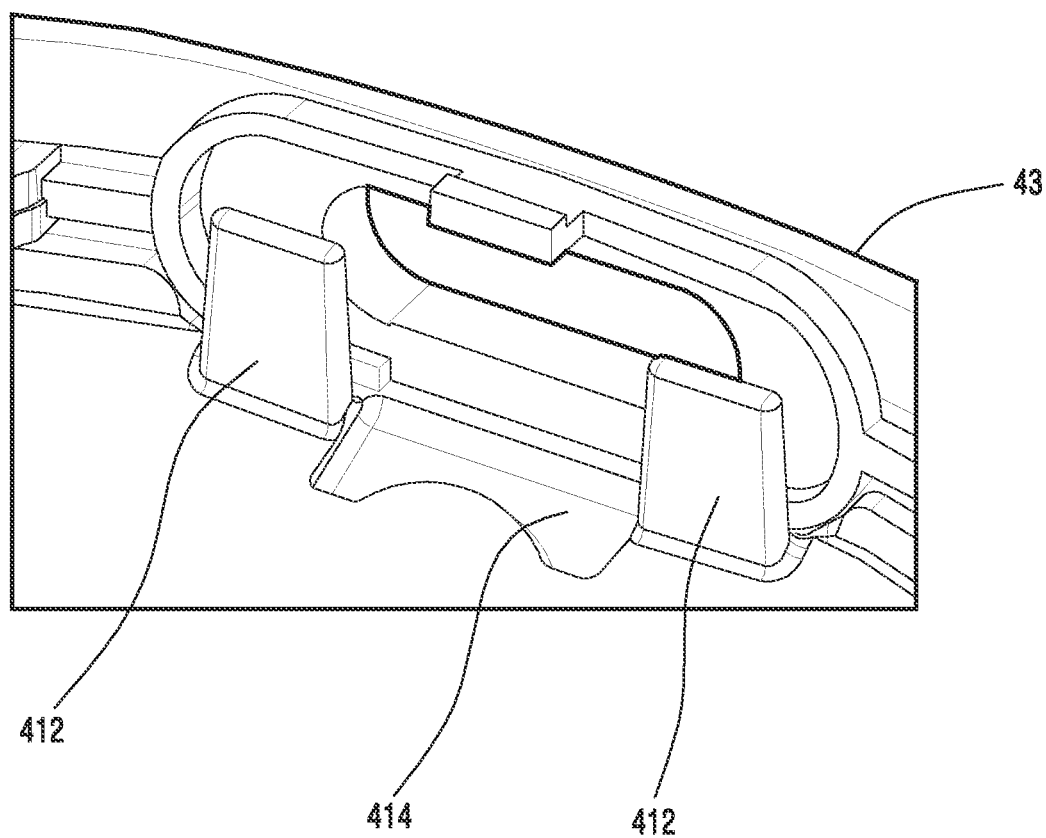
FIG. 24C is a perspective diagram illustrating a partial state of coupling a front case to a connection case according to various embodiments of the present disclosure.
Figure 25A:
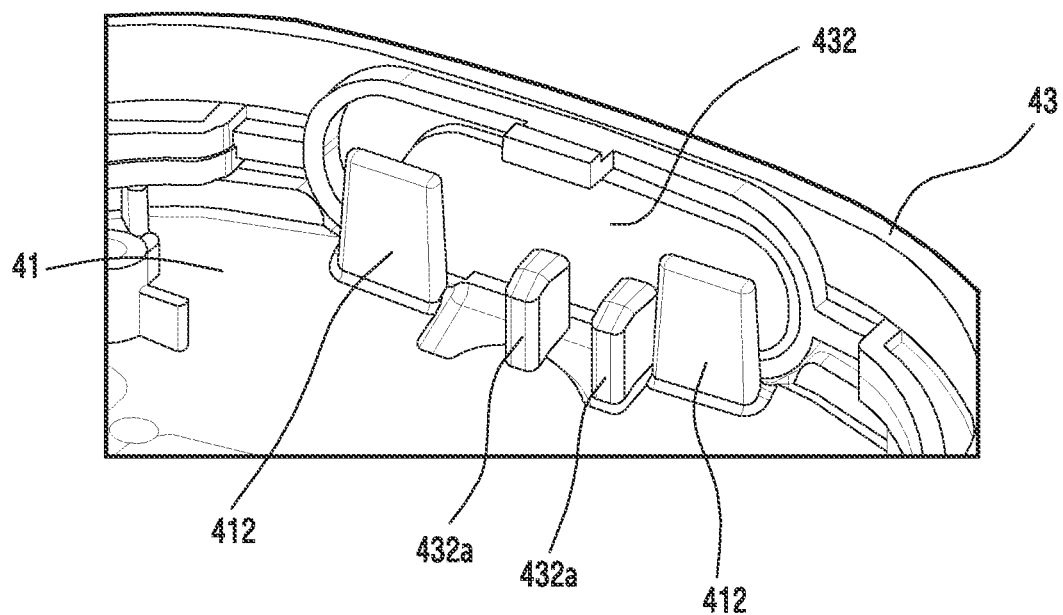
FIG. 25A is a perspective diagram illustrating a second side key in a state of coupling a front case to a connection case according to various embodiments of the present disclosure.
Figure 25B:
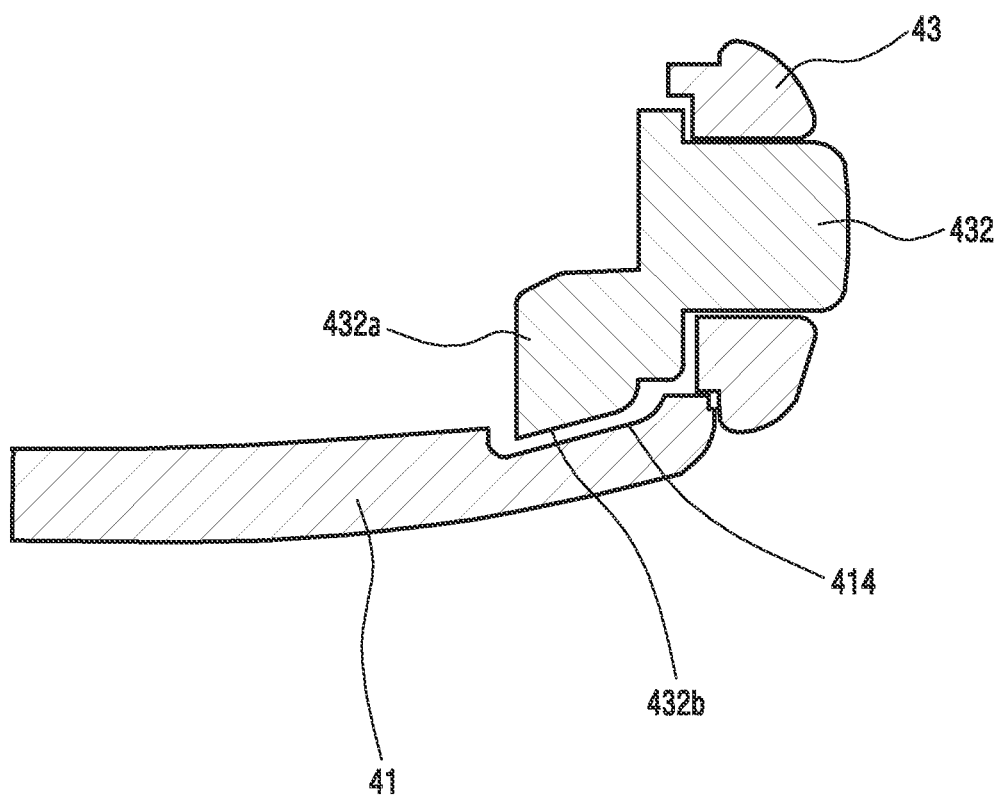
FIG. 25B is a cross section illustrating a mounting state of a second side key according to various embodiments of the present disclosure.

FIG. 24A is a perspective diagram illustrating a coupling structure of a second side key provided in a connection case according to various embodiments of the present disclosure. FIG. 24B is a perspective diagram illustrating a vertical wall and a recess provided in a front case according to various embodiments of the present disclosure. FIG. 24C is a perspective diagram illustrating a partial state of coupling the front case to the connection case according to various embodiments of the present disclosure. FIG. 25A is a perspective diagram illustrating the second side key in a state of coupling the front case to the connection case according to various embodiments of the present disclosure. FIG. 25B is a cross section illustrating a mounting state of the second side key according to various embodiments of the present disclosure.

Referring to FIGS. 24A to 25B, the wearable device according to various embodiments of the present disclosure may include the slide key 432 (i.e., the second side key) for powering On/Off or converting a service mode. The slide key 432 may have the second vertical wall 412 for preventing the floating of the key hole 430a of the connection case 43. The second vertical wall 412 may be formed in an inner surface of the front case 41 and may be configured to prevent separation of the assembled second side key 432 in accordance to coupling of the front case 41 and the connection case 43. In addition, the second vertical walls 412 may be configured in pair to face each other in a spaced-apart state. In addition, a recess 414 may be provided in a surface between the second vertical walls 412. The second side key 432 may further include a first rib 432a formed to protrude inwards in a rear surface and arranged between the second vertical walls 412, and a second rib 432b which is formed at an upper end of the first rib 432a and of which at least a portion is inserted into the recess 414 and movable. A portion of the second rib 432b is inserted into the recess 414 and moved, thereby being capable of preventing the floating of the second side key 432 and thus preventing malfunction.

Figure 26:
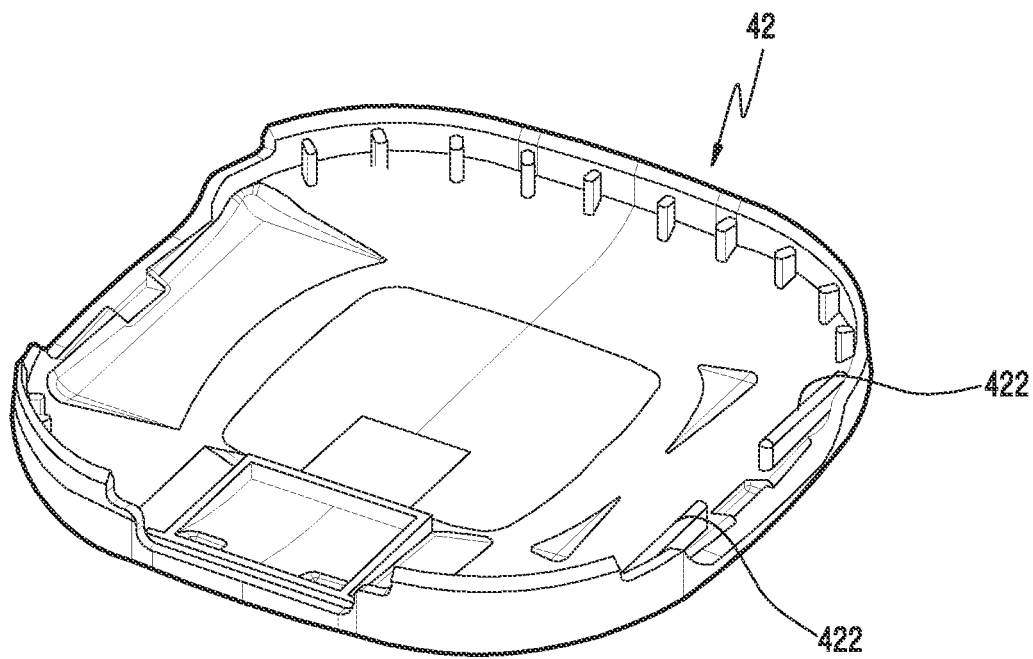
FIG. 26 is a cross section illustrating a rear case according to various embodiments of the present disclosure.

FIG. 26 is a cross section illustrating a rear case according to various embodiments of the present disclosure.

Figure 28A:
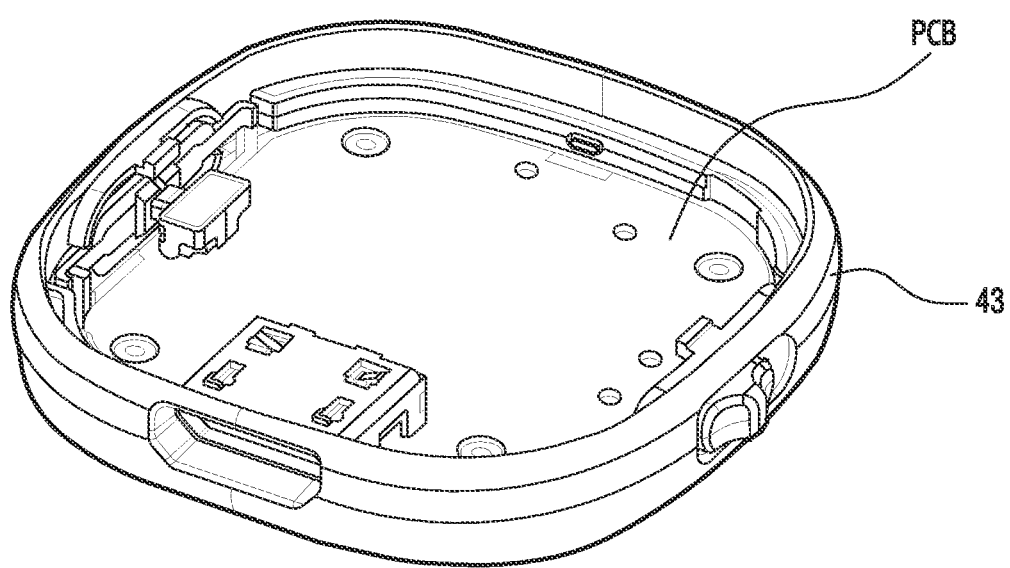
FIGS. 28A and 28B are perspective diagrams illustrating a body before battery mounting according to various embodiments of the present disclosure.
Figure 28B:
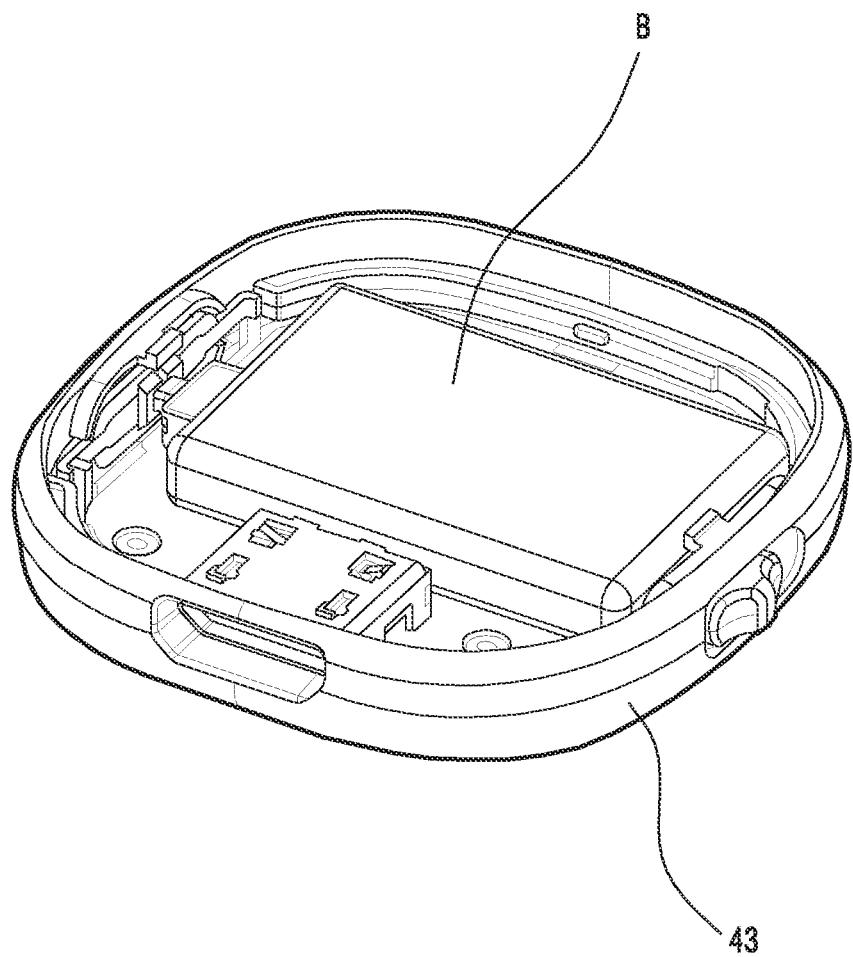

Referring to FIG. 26, the rear case 42 is installed to face a battery (B) (shown in FIGS. 28A and 28B). Thus, the rear case 42 may be dubbed a battery cover. As mentioned earlier, after the front case 41, the connection case 43, and a plurality of components are mounted, ultrasonic fusion is performed between the front case 41 and the connection case 43 and lastly the battery (B) is mounted and ultrasonic fusion may be performed between the connection case 43 and the rear case 42. A plurality of support walls 422 for preventing the floating of the mounted battery (B) may be formed in an inner surface of the rear case 42.

Figure 27A:
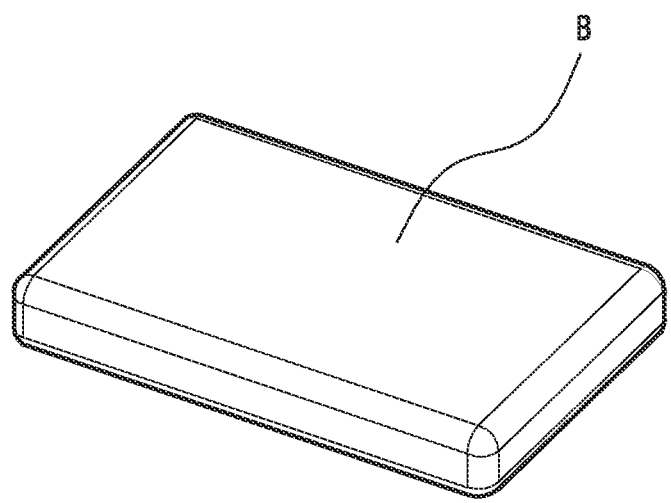
FIGS. 27A and 27B are perspective diagrams illustrating one or two batteries mounted according to various embodiments of the present disclosure.
Figure 27B:
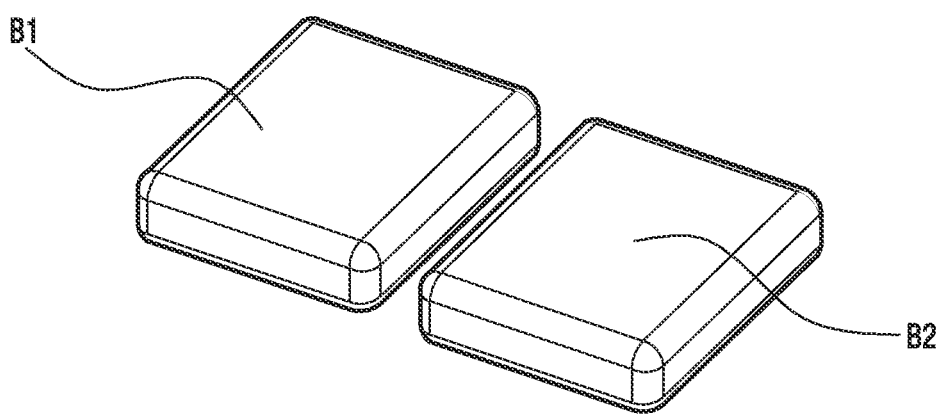

FIGS. 27A and 27B are perspective diagrams illustrating one or two batteries mounted according to various embodiments of the present disclosure.

FIGS. 28A and 28B are perspective diagrams illustrating a body before battery mounting according to various embodiments of the present disclosure.

Referring to FIG. 27A to FIG. 28B, assembly components such as batteries (B) or (B1), (B2) and the like may be mounted in a device of the semi-assembled state. These components may be electrically connected to one another by means of soldering, a connector, and the like, and may be arranged to be physically fixed by a tape, a bonding and the like.

As in various embodiments of the present disclosure, in many cases, commonly, the battery (B) of FIG. 27A occupies a wide area, so it is desirable to separately arrange fixed components (e.g., Surface Mounted Device (SMD) components) on one surface (i.e., an opposite surface of a battery mounting surface) of a PCB facing the front case so as to prevent the battery (B) from being damaged due to assembly deflection and interference. Besides the assembly order of the present embodiment of the present disclosure, it is possible to first assemble assembly components such as the battery (B) and the like before semi assembly. Though not illustrated, a plurality of small batteries (B1) and (B2) (shown in FIG. 27B) may be divided and mounted, whereby a charging device, various human body measurement sensors (e.g., Heart Rate Maximum (HRM) and the like may be efficiently installed in a secured region. The separating and mounting of the batteries B1 and B2 may be applied even to a curved wearable device of a flexible or curved form.

Figure 29:
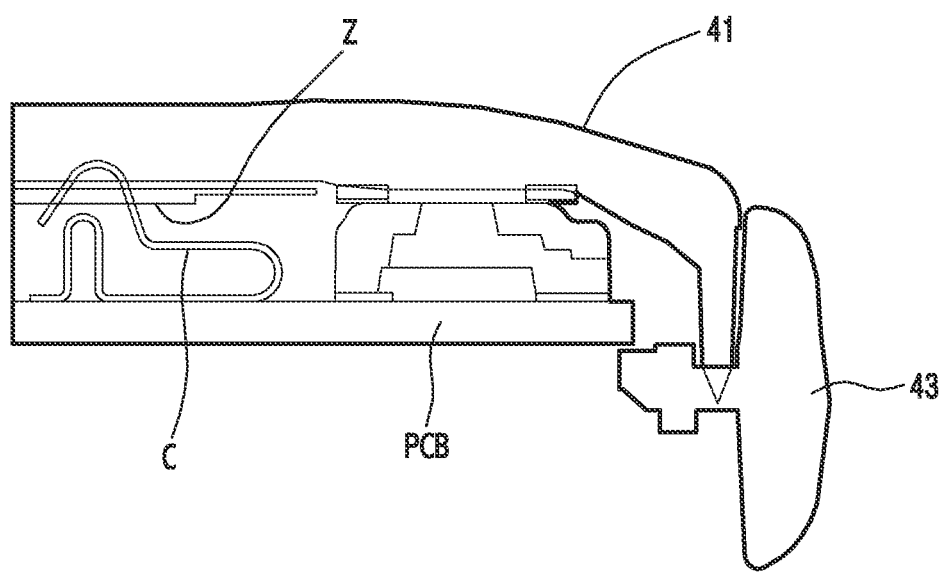
FIG. 29 is a perspective diagram illustrating a body after battery mounting according to various embodiments of the present disclosure.

FIG. 29 is a perspective diagram illustrating a body after battery mounting according to various embodiments of the present disclosure.

Referring to FIG. 29, various embodiments of the present disclosure include a structure of mounting a buzzer (Z) for forwarding a voice signal. For this, the buzzer (Z) may be attached to an inner surface of the front case 41, and may be electrically connected with a PCB which is spaced apart from the buzzer (Z) by an elastic type contact (C). Undoubtedly, even a method of soldering and connecting by a wire may be used. However, in many cases, even a space is not enough to fold and put the wire into the cases in a subminiature wearable device. Thus, it is more effective to use the elastic type contact (C) for the sake of assembly convenience.

At this time, the elastic type contact (C) exhibits effects of pushing out a counterpart piece by self-elasticity when the PCB is safely mounted. This deflection is easy to result in device damage upon assembly and poor performance after assembly. Thus, the present embodiment of the present disclosure designs to implement a separate fixing part inside the connection case 43 pre-assembled with the front case 41, to perform assembly after previously removing a repulsive force of an elastic component in a semi-assembled state. For this, elastic and compressive components are collectively mounted on one lateral surface (i.e., a surface of the front case 41 of the present embodiment of the present disclosure) of the PCB as mentioned earlier.

Figure 30:
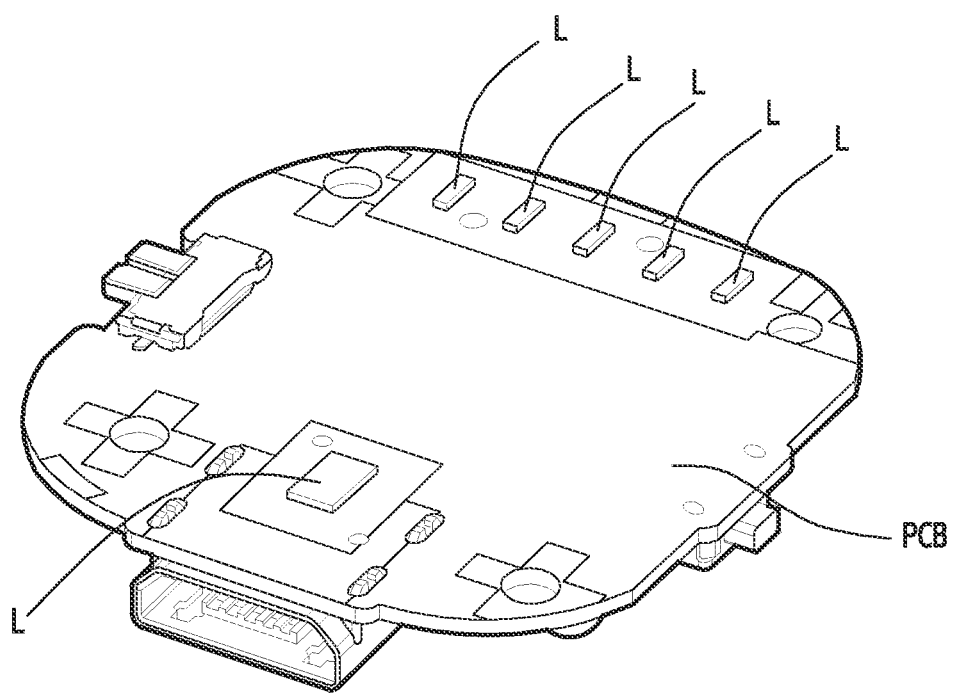
FIG. 30 is a perspective diagram illustrating Light Emitting Diodes (LEDs) installed in one surface of a PCB according to various embodiments of the present disclosure.

FIG. 30 is a perspective diagram illustrating LEDs installed in one surface of a PCB according to various embodiments of the present disclosure.

Figure 31:
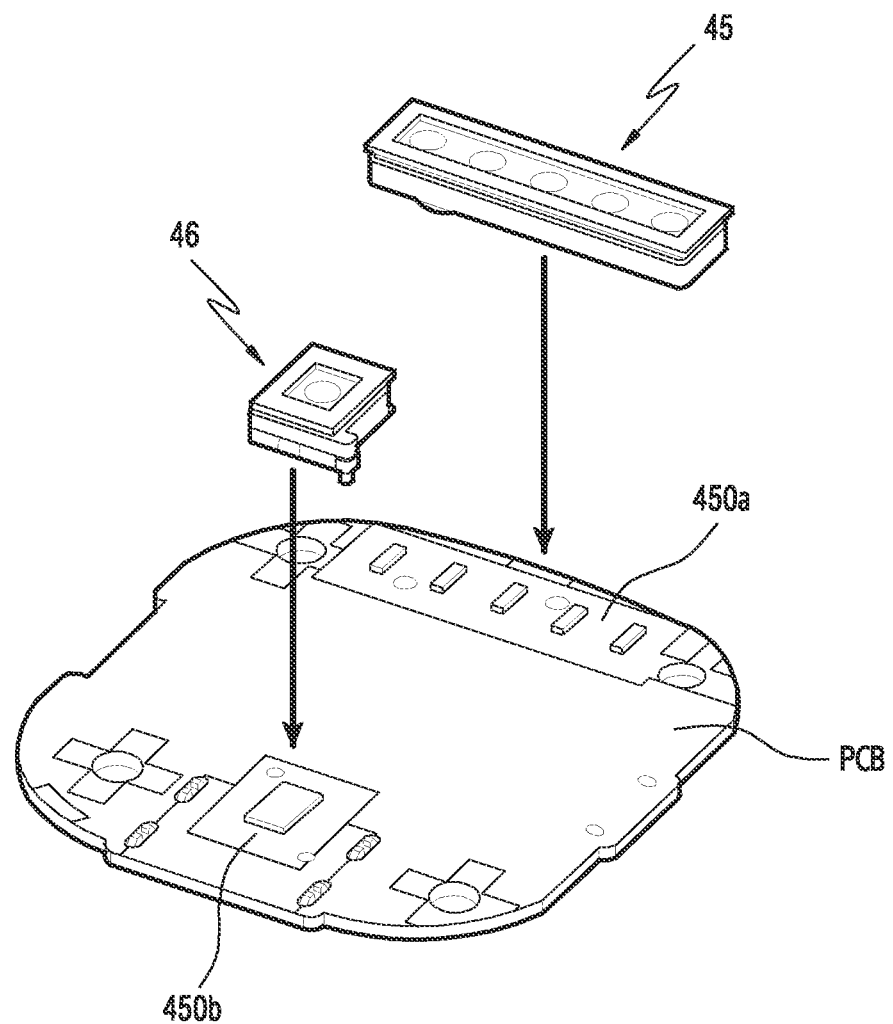
FIG. 31 is a perspective diagram illustrating an LED assembly of before installation in one surface of a PCB according to various embodiments of the present disclosure.

FIG. 31 is a perspective diagram illustrating an LED assembly of before installation in one surface of a PCB according to various embodiments of the present disclosure.

Figure 32:
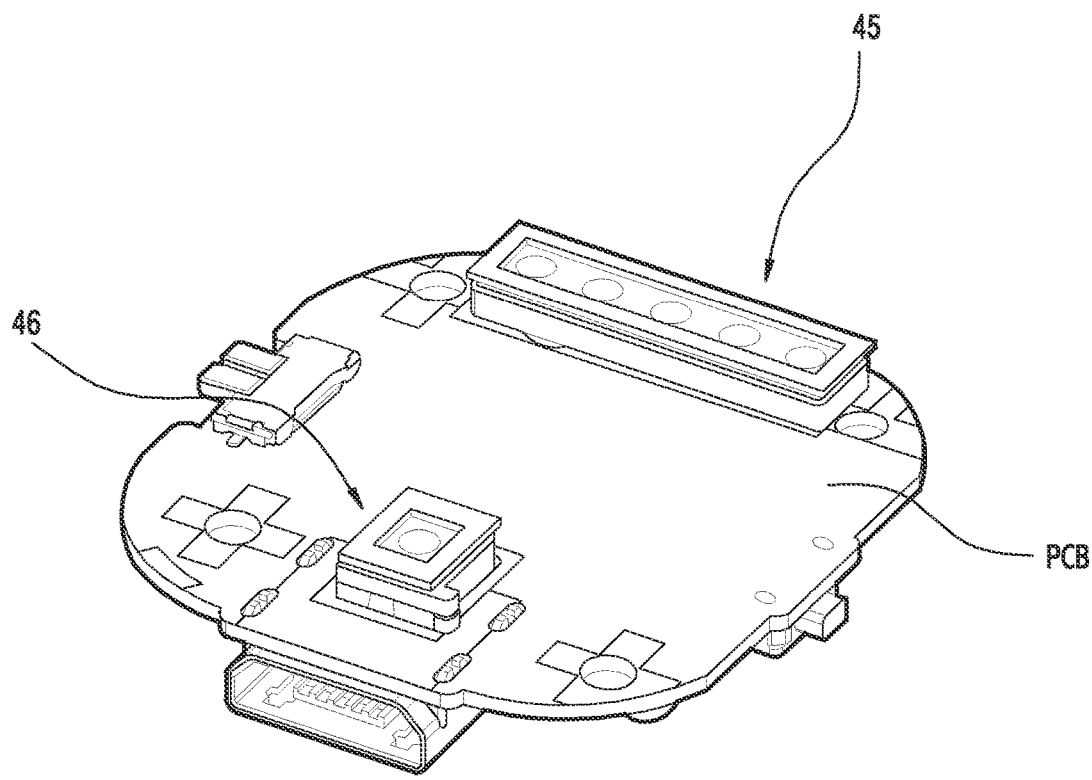
FIG. 32 is a perspective diagram illustrating an LED assembly of after installation in one surface of a PCB according to various embodiments of the present disclosure.

FIG. 32 is a perspective diagram illustrating an LED assembly of after installation in one surface of a PCB according to various embodiments of the present disclosure.

Figure 33:
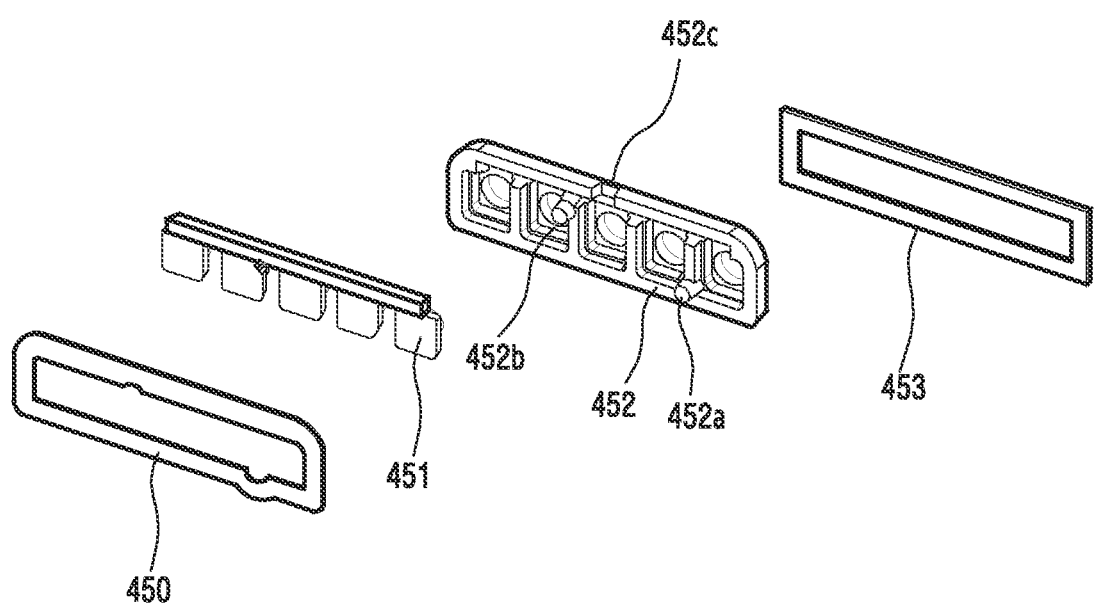
FIG. 33 is an exploded perspective diagram illustrating one LED assembly according to various embodiments of the present disclosure.

FIG. 33 is an exploded perspective diagram illustrating one LED assembly according to various embodiments of the present disclosure.

Referring to FIGS. 30 to 33, various embodiments of the present disclosure include a plurality of LED assemblies 45 and 46. The LED assembly 45 may include a sealing structure capable of preventing light leakage between LEDs (L) and the front case to forward a clear signal. The LED assembly 45 includes a semitransparent milky urethane 451 decreasing a hot spot, and a sealing part 452 of double-injected PC maintaining a form and preventing light leakage. The double-injection sealing part 452 may surround all of a circumference part excepting a light emitting part and at least a urethane injection gate 452*c* with PC so as to prevent light leakage, and may have guide poles 452*a* and 452*b* to align a position of the double-injection sealing part 452.

In addition, to prevent light leakage, the LED assembly 45 includes a shield tape 450 for fixing the PCB and a sponge 453 installed in a portion coming in touch with a housing of an upper side. This sealing structure comes in touch with an inner surface of the front case and thus, forwards a lighting signal to a user. In FIG. 31, reference numeral 450*a* denotes a shield surface of the LED assembly 46, and reference numeral 450*b* denotes a shield surface of the LED assembly 45.

Figure 34:
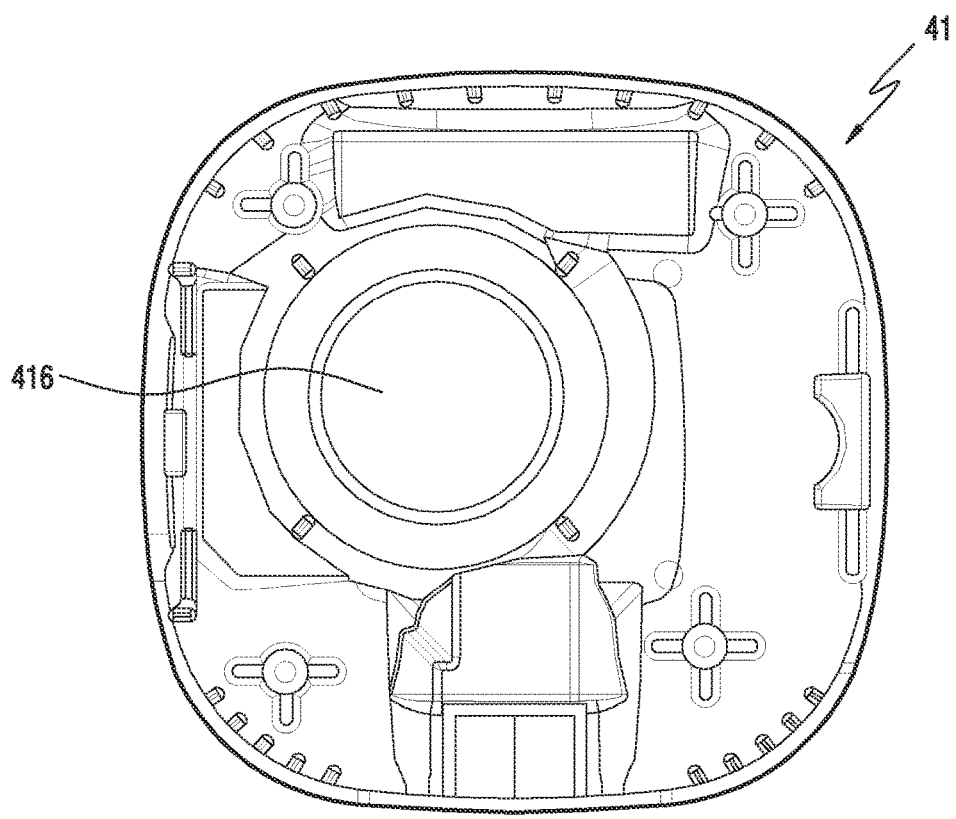
FIG. 34 is a plane diagram illustrating an inner surface of a front case according to various embodiments of the present disclosure.

FIG. 34 is a plane diagram illustrating an inner surface of a front case according to various embodiments of the present disclosure.

Figure 35A:
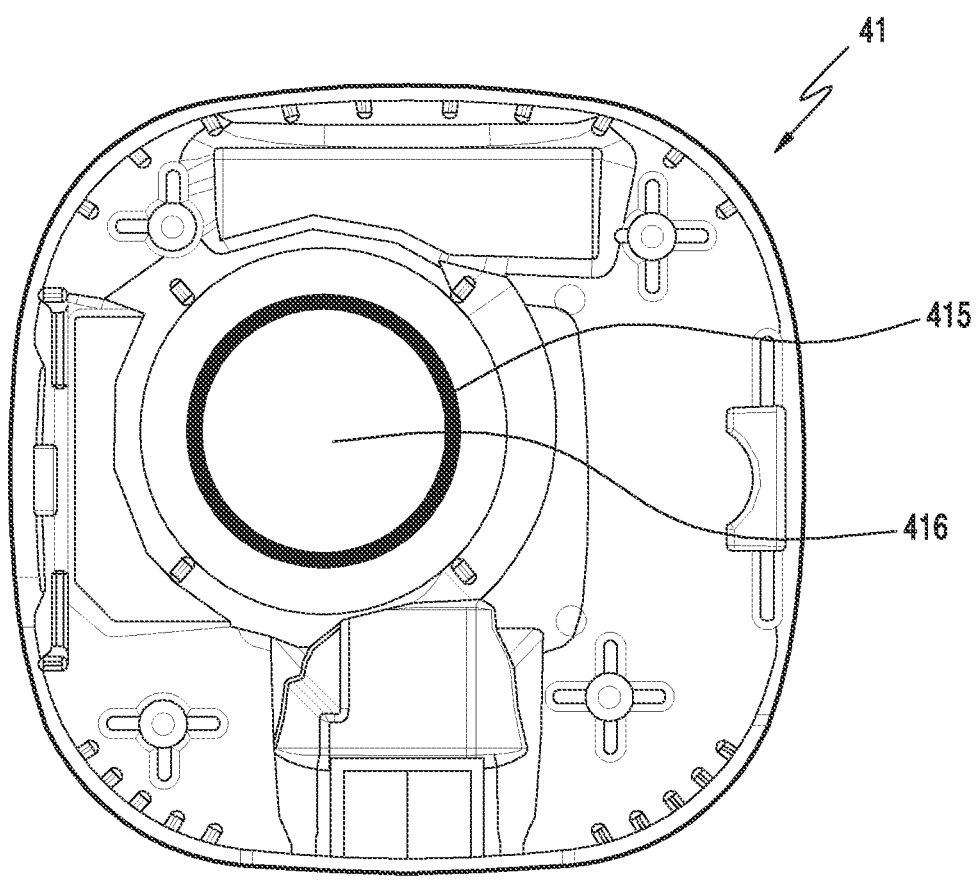
FIGS. 35A, 35B, and 35C are plane diagrams illustrating various modified examples of an attachment surface of a front case mounting a buzzer according to various embodiments of the present disclosure.
Figure 35B:
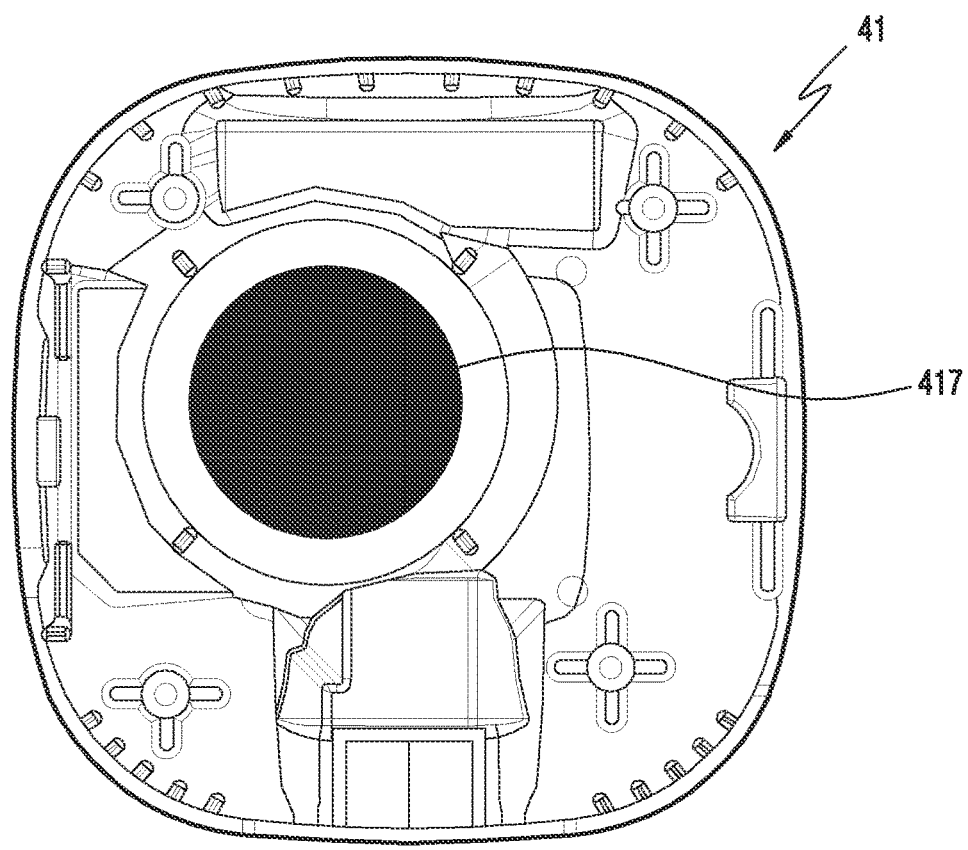
Figure 35C:
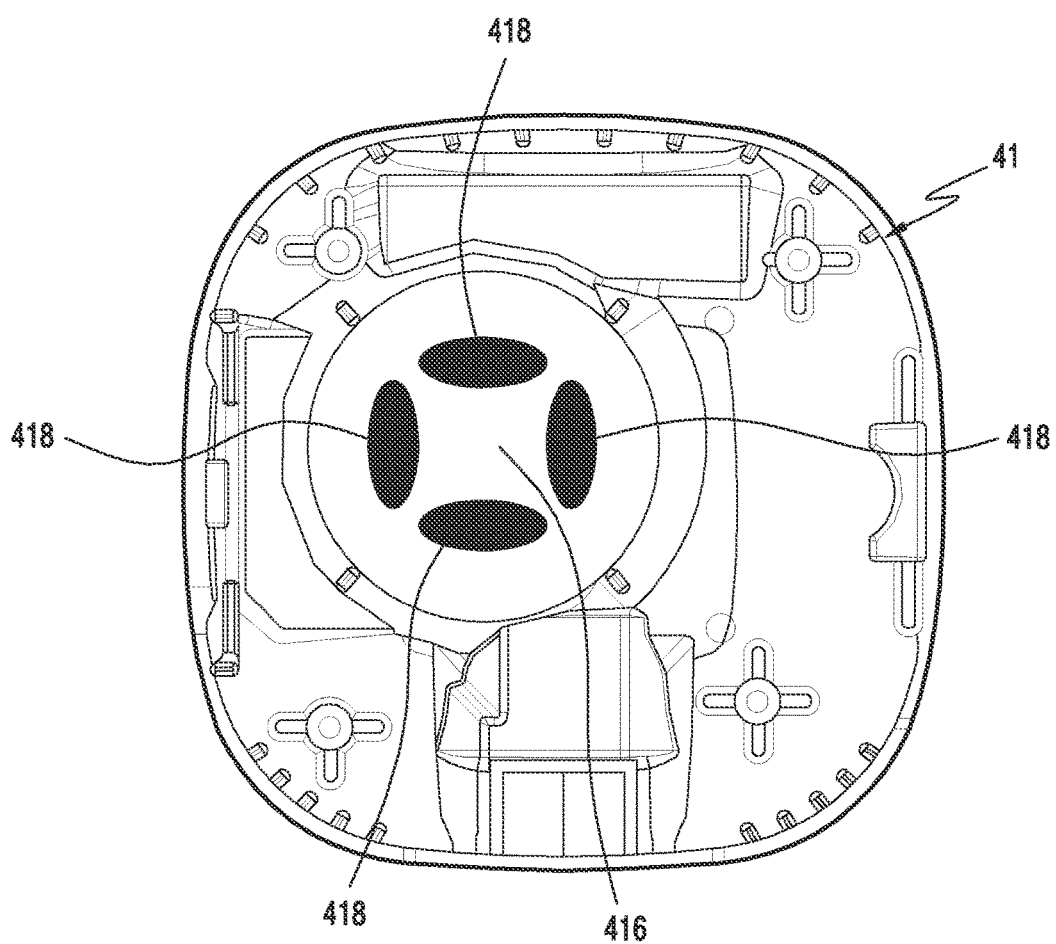

FIGS. 35A, 35B, and FIG. 35C are plane diagrams illustrating various modified examples of an attachment surface of a front case mounting a buzzer according to various embodiments of the present disclosure.

Referring to FIGS. 34 to 35C, if the buzzer (Z) is attached to an attachment surface 416 of an inner surface of the front case 41, a deflection of performance of the buzzer (Z) may occur depending on an attachment position and attachment strength of the buzzer (Z). The attachment of the buzzer (Z) may use a bonding and a tape. In various embodiments of the present disclosure, a buzzer mounting structure is described using a bonding. The attachment position of the buzzer (Z) may be controlled through a guide rib 415 formed around the buzzer (Z).

The attachment strength of the buzzer (Z) may be adjusted by controlling a bonding region. The attachment strength of the buzzer (Z) may be implemented basically by a method of controlling a discharge rate of a bonding dispenser and, upon buzzer attachment, controlling a degree of diffusing a bonding in a space between the buzzer (b) and the front case 41, and a structure of forming a channel at an expansion limit point of a boding region to prevent a phenomenon in which the boding is diffused beyond a designated region. In addition, the bonding expansion region may be controlled by means of a structure of concavely constructing 417 the whole inner side of the buzzer attachment surface 416 and forming one or a plurality of dimples 418.

Figure 36:
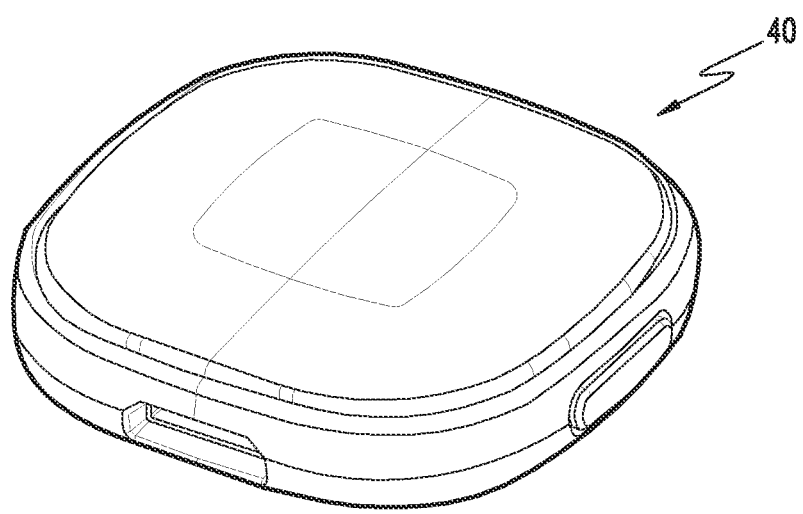
FIG. 36 is a perspective diagram illustrating a body of an LED On state according to various embodiments of the present disclosure.

FIG. 36 is a perspective diagram illustrating a body of an LED On state according to various embodiments of the present disclosure.

Referring to FIG. 36, if an LED turns on, light emitted from the LED is wave guided through a portion of the front case 41. Thus, a user may check information forwarded by the visibly emitted light.

As described above, a wearable device according to various embodiments of the present disclosure may seek a consumer's individuality because a wearing part is changeable in accordance with user's tastes.

In addition, the wearable device according to the various embodiments of the present disclosure may be safely worn on clothes and the like.

In addition, the wearable device according to the various embodiments of the present disclosure may provide the directivity of coupling and separation of a body.

According to various embodiments of the present disclosure, at least part of an apparatus (e.g., modules or functions thereof) or method (e.g., operations) according to the present disclosure may be, for example, implemented by an instruction stored in a computer-readable storage media in a form of a programming module. In a case where the instruction is executed by one or more processors, the one or more processors may perform functions corresponding to the instructions. The computer-readable storage media may be, for example, the memory 130A. At least part of the programming module may be, for example, implemented (e.g., executed) by the processor 120A. At least part of the programming module may include, for example, modules, programs, routines, sets of instructions, processes or the like for performing one or more functions.

The computer-readable recording media may include a magnetic media such as a hard disk, a floppy disk, and a magnetic tape, an optical media such as a Compact Disc Read Only Memory (CD-ROM) and a Digital Versatile Disc (DVD), a Magneto-Optical Media such as a floptical disk, and a hardware device specially configured to store and perform a program instruction (e.g., the programming module) such as a ROM, a Random Access Memory (RAM), a flash memory and the like. In addition, the program instruction may include not only a mechanical code such as a code made by a compiler but also a high-level language code executable by a computer using an interpreter and the like. The aforementioned hardware device may be configured to operate as one or more software modules in order to perform an operation of the present disclosure, and vice versa.

The module or the programming module according to the present disclosure may include at least one or more of the aforementioned constituent elements, or omit some of the aforementioned constituent elements, or further include additional other constituent elements. Operations carried out by the module, the programming module or the other constituent elements according to the present disclosure may be executed in a sequential, parallel, repeated or heuristic method. In addition, some operations may be executed in different order or may be omitted, or other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A wearable device comprising:
a clip type wearing part comprising:
a first opening including a circumference and a bottom,
a second opening substantially opposite the first opening, and
a safe mounting part; and
a body configured to fit to and separate from the clip type wearing part,
wherein the safe mounting part is shaped and configured to:
cover the circumference and the bottom of the first opening, and
securely receive the body, and
wherein at least a portion of the second opening is formed in the safe mounting part.

2. The wearable device of claim 1,
wherein the first opening is configured to be opened in an upward orientation, and
wherein the second opening is configured to be opened in a downward orientation in the bottom of the safe mounting part.

3. The wearable device of claim 2, wherein the second opening is configured to be insertable in at least a portion of the wearing part.

4. The wearable device of claim 2, further comprising:
an anti-sliding member,
wherein the second opening is configured to include a box shape, and
wherein the anti-sliding member is configured to be coupled to the second opening.

5. The wearable device of claim 1, further comprising:
a clip part,
wherein the clip type wearing part includes the clip part such that the wearable device can be attachable to clothing,
wherein the clip part comprises:
a first material part, and
a second material part different from the first material part,
wherein the first material part comprises a hard material comprising a metal material,
wherein the second material part comprises a soft material softer than the hard material, and
wherein the second material is configured to cover the first material part.

6. The wearable device of claim 5,
wherein the clip part includes an end region,
wherein the end region comprises a protrusion rib which is closely adhered to the second opening,
wherein at least a portion of the end region is insertable into the second opening, and
wherein an end of the protrusion rib is configured to include a structure in which at least a portion of the end of the protrusion rib is overlapped with a bottom portion of the wearing part.

7. The wearable device of claim 1, wherein the body comprises:
a front case of including a portion that performs a display function,
a battery case,
a connection case configured to be coupled with the front case and the battery cases; and
a main printed circuit board (PCB) mounted by a coupling structure of the front case and the connection case,
wherein the PCB comprises at least one surface-mount device (SMD) component having elasticity positioned on an upper surface of the PCB,
wherein the PCB comprises:
an interface part connector, and at least one battery positioned on a lower surface of the PCB, and wherein the connection case includes at least one side key mounted therein.

8. The wearable device of claim 7, wherein the component having the elasticity comprises at least one sealing member, or wherein the component having the elasticity comprises a plurality of mounted light emitting diodes (LEDs), the LEDs being arranged to face at least a portion of the front case, and the LEDs being light wave guided.

* * * * *